US009161865B2

(12) United States Patent
Paveletzke et al.

(10) Patent No.: US 9,161,865 B2
(45) Date of Patent: Oct. 20, 2015

(54) ABSORBENT ARTICLE

(71) Applicant: Kimberly-Clark Worldwide, Inc., Neenah, WI (US)

(72) Inventors: Julie Ann Paveletzke, Appleton, WI (US); John Timothy Hahn, Merrill, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 259 days.

(21) Appl. No.: 13/853,701

(22) Filed: Mar. 29, 2013

(65) Prior Publication Data

US 2014/0296816 A1    Oct. 2, 2014

(51) Int. Cl.
*A61F 13/15* (2006.01)
*A61F 13/493* (2006.01)
*A61F 13/49* (2006.01)
*A61F 13/64* (2006.01)
*A61F 13/56* (2006.01)

(52) U.S. Cl.
CPC ........... *A61F 13/493* (2013.01); *A61F 13/4906* (2013.01); *A61F 13/49017* (2013.01); *A61F 13/5655* (2013.01); *A61F 13/64* (2013.01); *A61F 2013/5688* (2013.01)

(58) Field of Classification Search
CPC ................. A61F 13/5655; A61F 13/64; A61F 2013/5688
See application file for complete search history.

(56) References Cited

U.S. PATENT DOCUMENTS

| 2,573,903 | A | 11/1951 | Frances |
| 3,776,232 | A | 12/1973 | Schaar |
| 4,210,143 | A | 7/1980 | De Jonckheere |
| 4,753,650 | A | 6/1988 | Williams |
| 4,850,988 | A | 7/1989 | Aledo et al. |
| 4,850,992 | A | 7/1989 | Amaral et al. |
| 4,883,481 | A | 11/1989 | Blanchard |
| 5,040,244 | A | 8/1991 | Tubbs |
| 5,944,707 | A | 8/1999 | Ronn |
| 6,287,287 | B1 | 9/2001 | Elsberg |
| 6,551,294 | B1 | 4/2003 | Elsberg et al. |
| 6,572,601 | B2 | 6/2003 | Suprise et al. |
| 6,764,478 | B2 | 7/2004 | Ashton et al. |
| 7,575,573 | B1 | 8/2009 | Roe et al. |
| 8,398,605 | B2 | 3/2013 | Roe et al. |
| 2005/0038400 | A1 | 2/2005 | Poruthoor |
| 2005/0222549 | A1 | 10/2005 | Balogh |
| 2009/0187156 | A1 | 7/2009 | Anzalone |
| 2009/0240228 | A1 | 9/2009 | Nonnenmann et al. |

FOREIGN PATENT DOCUMENTS

| CA | 493293 A | 6/1953 |
| GB | 0665724 A | 1/1952 |
| GB | 2468724 A | 9/2010 |
| WO | WO 97/25951 A1 | 7/1997 |

*Primary Examiner* — Jacqueline Stephens
(74) *Attorney, Agent, or Firm* — Kimberly-Clark Worldwide, Inc.

(57) ABSTRACT

An absorbent article having improved handling of body exudates. The absorbent article can have a pair of leg opening adjustment mechanisms which a user of the absorbent article can independently adjust to provide a desired tension and/or closure of the absorbent article about the legs of the wearer of the absorbent article.

19 Claims, 8 Drawing Sheets

ABSORBENT ARTICLE

BACKGROUND

Personal care absorbent articles, such as diapers, are generally categorized and sized according to the weight of the intended wearer of the absorbent article. A primary function of personal care absorbent articles is to absorb and retain body exudates, such as urine and fecal material, with additional desired attributes including low leakage of the body exudates from the absorbent article and a dry feel to the wearer of the absorbent article. To accomplish these tasks, personal care absorbent articles generally have components such as a waist fastening system, elastic leg cuffs, and elastic waistbands.

A good fit of the personal care absorbent article, such as a diaper, can be found when a snug fit of the absorbent article on the wearer does not leave gaps between the absorbent article and the skin of the wearer and does not leave indentations on the skin of the wearer upon removal of the absorbent article. How well the absorbent article fits at the waist and leg openings depends to a great degree upon the ratio of the waist circumference to the leg circumference of the wearer of the absorbent article. If a wearer, such as a baby, has a large ratio of waist circumference to leg circumference, the large ratio will prevent the absorbent article, such as a diaper, from obtaining a snug fit at the leg opening without over tightening the diaper at the waist. If the ratio of waist circumference to leg circumference is low, the opposite will be true. An additional situation which can result in poor fit of the absorbent article can occur when a wearer of the absorbent article experiences rapid change in body shape without an overall change in weight. Such changes in body shape can result in poor fit of the absorbent articles about the legs of the wearer. An absorbent article, therefore, that fits the wearer early on may no longer fit correctly in the legs even though the weight of the wearer has not changed and the absorbent article is sized for the weight of the wearer. A poor fit of the absorbent article can result in leakage of body exudates from the absorbent article.

The waist fastening system, elastic leg cuffs, and elastic waist bands have been provided to absorbent articles in an effort to minimize leakage of body exudates from the absorbent articles. Manufacturers, however, generally set the tension in the elastic leg cuffs and waist bands and then place each out of reach of the user, such as a diaperer or wearer. The user of the absorbent article, therefore, has generally been unable to tighten or loosen the elastic leg cuffs and waist bands because of their construction.

There is a need for an absorbent article which can provide a better fit of the absorbent article about the legs of the wearer. There is a need for an absorbent article which can allow the user to adjust the fit of the absorbent article about the wearer of the absorbent article. There is a need for an absorbent article which can allow for independent adjustment of the leg openings of the absorbent article.

SUMMARY

In an embodiment, an absorbent article can comprise a longitudinal direction and a lateral direction; a pair of longitudinal side edges; a body facing liner; a backsheet comprising a body facing surface and a garment facing surface; a pair of leg opening adjustment mechanisms positioned on the body facing surface of the backsheet and each leg opening adjustment mechanism which can comprise a cover comprising two longitudinal direction edges and two lateral direction edges and an adjustment member comprising a bonded end and an unbonded end; a pair of leg elastic members; and an absorbent body positioned between the body facing liner and the backsheet. In an embodiment, both of the longitudinal direction edges of the cover and at least one of the lateral direction edges of the cover can be bonded to the body facing surface of the backsheet. In an embodiment, the leg opening adjustment mechanisms can be positioned laterally inward of the longitudinal side edges. In an embodiment, the leg elastic members can be positioned laterally inward of the longitudinal side edges. In an embodiment, the leg opening adjustment mechanisms can partially overlap the leg elastic members. In an embodiment, the leg elastic members can be closer in proximity to the longitudinal side edges than the leg opening adjustment mechanisms. In an embodiment, the leg opening adjustment mechanisms can be closer in proximity to the longitudinal side edges than the leg elastic members. In an embodiment, the backsheet can further comprise an opening through which the unbonded end of the adjustment member can extend. In an embodiment, the adjustment member can further comprise a grasping tab, the grasping tab comprising fasteners. In an embodiment, the leg opening adjustment mechanisms can be positioned laterally outward of the absorbent body.

In an embodiment, an absorbent article can comprise a longitudinal direction and a lateral direction; a pair of longitudinal side edges; a body facing liner; a backsheet comprising a body facing surface and a garment facing surface; a pair of leg opening adjustment mechanisms positioned on the garment facing surface of the backsheet and each leg opening adjustment mechanism can comprise a cover comprising two longitudinal direction edges and two lateral direction edges and an adjustment member comprising a bonded end and an unbonded end; a pair of leg elastic members; and an absorbent body positioned between the body facing liner and the backsheet. In an embodiment, both of the longitudinal direction edges of the cover and at least one of the lateral direction edges of the cover can be bonded to the garment facing surface of the backsheet. In an embodiment, the leg opening adjustment mechanisms can be positioned laterally inward of the longitudinal side edges. In an embodiment, the leg elastic members can be positioned laterally inward of the longitudinal side edges. In an embodiment, the leg opening adjustment mechanisms can partially overlap the leg elastic members. In an embodiment, the leg elastic members can be closer in proximity to the longitudinal side edges than the leg opening adjustment mechanisms. In an embodiment, the leg opening adjustment mechanisms can be closer in proximity to the longitudinal side edges than the leg elastic members. In an embodiment, the adjustment member can further comprise a grasping tab, the grasping tab comprising fasteners. In an embodiment, the leg opening adjustment mechanisms can be positioned laterally outward of the absorbent body.

DETAILED DESCRIPTION

Figure 1:
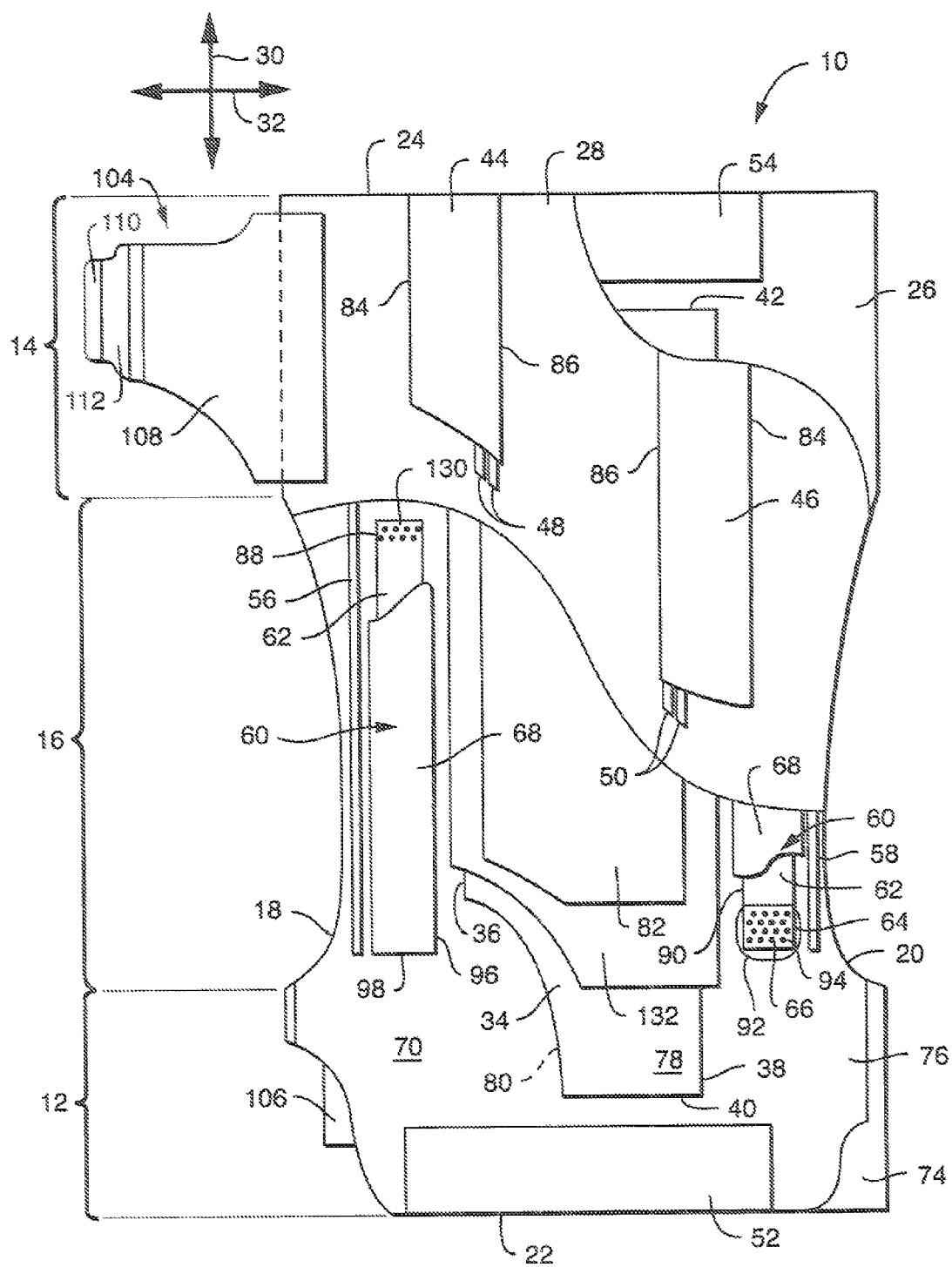
FIG. 1 is a plan view of a non-limiting illustration of an absorbent article, such as, for example, a diaper, in an unfastened, stretched and laid flat condition with the surface of the absorbent article which contacts the wearer facing the viewer and with portions cut away for clarity of illustration.

In an embodiment, the present disclosure is generally directed towards an absorbent article which can have improved management of body exudates. In an embodiment, the present disclosure is generally directed towards an absorbent article which can provide a better fit of the absorbent article about the legs of the wearer of the absorbent article. In an embodiment, the present disclosure is generally directed towards an absorbent article which can be adjusted to provide a desired tension or closure of the absorbent article about the legs of the wearer of the absorbent article. In an embodiment, the present disclosure is generally directed towards an absorbent article which can have leg opening adjustment mechanisms. In an embodiment, the present disclosure is directed towards an absorbent article which can have leg elastic members and leg opening adjustment mechanisms. In such an embodiment, the leg elastic members can provide an initial barrier to leakage of body exudates from the absorbent article as the leg elastic members can provide an initial tensioning and closure of the leg openings about the legs of the wearer of the absorbent article. The provision of the leg opening adjustment mechanisms can allow for further tensioning and closure of the leg openings about the legs of the wearer of the absorbent article as deemed suitable by a user. The combination of the leg elastic members and the leg opening adjustment mechanisms can, therefore, reduce and/or eliminate leakage of body exudates from the absorbent article and can provide for customizable fit of the absorbent article about the legs of the wearer of the absorbent article.

Definitions:

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements. The bonding of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "fluid entangling" and "fluid entangled" refers herein to a formation process for further increasing the degree of fiber entanglement within a given fibrous nonwoven web or between fibrous nonwoven webs and other materials so as to make the separation of the individual fibers and/or the layers more difficult as a result of the entanglement. Generally this is accomplished by supporting the fibrous nonwoven web on some type of forming or carrier surface which has at least some degree of permeability to the impinging pressurized fluid. A pressurized fluid stream (usually multiple streams) can then be directed against the surface of the nonwoven web which is opposite the supported surface of the web. The pressurized fluid contacts the fibers and forces portions of the fibers in the direction of the fluid flow thus displacing all or a portion of a plurality of the fibers towards the supported surface of the web. The result is a further entanglement of the fibers in what can be termed the Z-direction of the web (its thickness) relative to its more planar dimension, its X-Y plane. When two or more separate webs or other layers are placed adjacent one another on the forming/carrier surface and subjected to the pressurized fluid, the generally desired result is that some of the fibers of at least one of the webs are forced into the adjacent web or layer thereby causing fiber entanglement between the interfaces of the two surfaces so as to result in the bonding or joining of the webs/layers together due to the increased entanglement of the fibers. The degree of bonding or entanglement will depend on a number of factors including, but not limited to, the types of fibers being used, the fiber lengths, the degree of pre-bonding or entanglement of the web or webs prior to subjection to the fluid entangling process, the type of fluid being used (liquids, such as water, steam or gases, such as air), the pressure of the fluid, the number of fluid streams, the speed of the process, the dwell time of the fluid and the porosity of the web or webs/other layers and the forming/carrier surface. One of the most common fluid entangling processes is referred to as hydroentangling which is a well-known process to those of ordinary skill in the art of nonwoven webs. Examples of fluid entangling process can be found in U.S. Pat. No. 4,939,016 to Radwanski et al., U.S. Pat. No. 3,485,706 to Evans, and U.S. Pat. Nos. 4,970,104 and 4,959,531 to Radwanski, each of which is incorporated herein in its entirety by reference thereto for all purposes.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" refers herein to one who fits an absorbent article, such as, but not limited to, a diaper, training pant, youth pant, incontinent product, or other absorbent article about the wearer of one of these absorbent articles. A user and a wearer can be one and the same person.

Absorbent Article:

Referring to FIG. 1, a non-limiting illustration of an absorbent article 10, such as, for example, a diaper, is illustrated in a top down view with portions cut away for clarity of illustration. While the embodiments and illustrations described herein may generally apply to absorbent articles manufactured in the product longitudinal direction, which is hereinafter called the machine direction manufacturing of a product, it should be noted that one of ordinary skill could apply the information herein to absorbent articles manufactured in the latitudinal direction of the product which hereinafter is called the cross direction manufacturing of a product without departing from the spirit and scope of the disclosure. The absorbent article 10 illustrated in FIG. 1 includes a front waist region 12, a back waist region 14, and a crotch region 16 interconnecting the front and back waist regions, 12 and 14, respectively. The absorbent article 10 has a pair of longitudinal side edges, 18 and 20, and a pair of opposite waist edges, respectively designated front waist edge 22 and back waist edge 24. The front waist region 12 can be contiguous with the front waist edge 22 and the back waist region 14 can be contiguous with the back waist edge 24.

The absorbent article 10 can include a backsheet 26 and a body facing liner 28. In an embodiment, the body facing liner 28 can be bonded to the backsheet 26 in a superposed relation by any suitable means such as, but not limited to, adhesives, ultrasonic bonds, thermal bonds, pressure bonds, or other conventional techniques. The backsheet 26 can define a length, or longitudinal direction 30, and a width, or lateral direction 32, which, in the illustrated embodiment, can coincide with the length and width of the absorbent article 10.

An absorbent body 34 can be disposed between the backsheet 26 and the body facing liner 28. The absorbent body 34 can have longitudinal edges, 36 and 38, which, in an embodiment, can form portions of the longitudinal side edges, 18 and 20, respectively, of the absorbent article 10 and can have opposite end edges, 40 and 42, which, in an embodiment, can form portions of the waist edges, 22 and 24, respectively, of the absorbent article 10. In an embodiment, the absorbent body 34 can have a length and width that are the same as or less than the length and width of the absorbent article 10. In an embodiment, a pair of containment flaps, 44 and 46, can be present and can inhibit the lateral flow of body exudates.

The front waist region 12 can include the portion of the absorbent article 10 that, when worn, is positioned at least in part on the front of the wearer while the back waist region 14 can include the portion of the absorbent article 10 that, when worn, is positioned at least in part on the back of the wearer. The crotch region 16 of the absorbent article 10 can include the portion of the absorbent article 10, that, when worn, is positioned between the legs of the wearer and can partially cover the lower torso of the wearer. The waist edges, 22 and 24, of the absorbent article 10 are configured to encircle the waist of the wearer and together define the central waist opening. Portions of the longitudinal side edges, 18 and 20, in the crotch region 16 can generally define leg openings when the absorbent article 10 is worn.

The absorbent article 10 can be configured to contain and/or absorb liquid, solid, and semi-solid body exudates discharged from the wearer. For example, containment flaps, 44 and 46, can be configured to provide a barrier to the lateral flow of body exudates. A flap elastic member, 48 and 50, can be operatively joined to each containment flap, 44 and 46, in any suitable manner known in the art. The elasticized containment flaps, 44 and 46, can define a partially unattached edge that can assume an upright configuration in at least the crotch region 16 of the absorbent article 10 to form a seal against the wearer's body. The containment flaps, 44 and 46, can be located along the absorbent article 10 longitudinal side edges, 18 and 20, and can extend longitudinally along the entire length of absorbent article 10 or can extend partially along the length of the absorbent article 10. Suitable construction and arrangements for containment flaps, 44 and 46, are generally well known to those skilled in the art and are described in U.S. Pat. No. 4,704,116 issued Nov. 3, 1987, to Enloe and U.S. Pat. No. 5,562,650 issued Oct. 8, 1996 to Everett et al., which are incorporated herein by reference.

To further enhance containment and/or absorption of body exudates, the absorbent article 10 can suitably include a front waist elastic member 52, a back waist elastic member 54, and leg elastic members, 56 and 58, as are known to those skilled in the art. The waist elastic members, 52 and 54, can be attached to the backsheet 26 and/or the body facing liner 28 along the opposite waist edges, 22 and 24, and can extend over part or all of the waist edges, 22 and 24. The leg elastic members, 56 and 58, can be attached to the backsheet 26 and/or the body facing liner 28 along the opposite longitudinal side edges, 18 and 20, and positioned in the crotch region 16 of the absorbent article 10.

The absorbent article 10 can further include a pair of leg opening adjustment mechanisms 60. The leg opening adjustment mechanisms 60 can include adjustment members 62 and a cover 68. In an embodiment, such as illustrated in the non-limiting illustration of FIG. 1, the leg opening adjustment mechanisms 60 can be positioned on the body facing surface 70 of the backsheet 26. In an embodiment, such as illustrated in the non-limiting illustration of FIG. 7, the leg opening adjustment mechanisms 60 can be positioned on the garment facing surface 72 of the backsheet 26.

Additional details regarding each of these elements of the absorbent article 10 described herein can be found below and with reference to the FIGS. 1 through 8.

Backsheet:

The backsheet 26 can be breathable and/or liquid impermeable. The backsheet 26 can be elastic, stretchable or non-stretchable. The backsheet 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the backsheet 26 can be constructed of a microporous polymeric film, such as polyethylene or polypropylene.

In an embodiment, the backsheet 26 can be a single layer of a liquid impermeable material. In an embodiment, the backsheet 26 can be suitably stretchable, and more suitably elastic, in at least the lateral or circumferential direction 32 of the absorbent article 10. In an embodiment, the backsheet 26 can be stretchable, and more suitably elastic, in both the lateral 32 and the longitudinal 30 directions. In an embodiment, the backsheet 26 can be a multi-layered laminate in which at least one of the layers is liquid impermeable. In an embodiment, the backsheet 26 may be a two layer construction, including an outer layer 74 material and an inner layer 76 material which can be bonded together such as by a laminate adhesive. Suitable laminate adhesives can be applied continuously or intermittently as beads, a spray, parallel swirls, or the like. Suitable adhesives can be obtained from Bostik Findlay Adhesives, Inc. of Wauwatosa, Wis., U.S.A. It is to be understood that the inner layer 76 can be bonded to the outer layer 74 utilizing ultrasonic bonds, thermal bonds, pressure bonds, or the like.

The outer layer 74 of the backsheet 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer 74 of a backsheet 26 can be a 20 gsm spunbond polypropylene non-woven web. The outer layer 74 may also be constructed of the same materials from which the body facing liner 28 can be constructed as described herein.

The liquid impermeable inner layer 76 of the backsheet 26 (or the liquid impermeable backsheet 26 where the backsheet 26 is of a single-layer construction) can be either vapor permeable (i.e., "breathable") or vapor impermeable. The liquid impermeable inner layer 76 (or the liquid impermeable backsheet 26 where the backsheet 26 is of a single-layer construction) may be manufactured from a thin plastic film, although other liquid impermeable materials may also be used. The liquid impermeable inner layer 76 (or the liquid impermeable backsheet 26 where the backsheet 26 is of a single-layer construction) can inhibit liquid body exudates from leaking out of the absorbent article 10 and wetting articles, such as bed sheets and clothing, as well as the wearer and caregiver. An example of a material for a liquid impermeable inner layer 76 (or the liquid impermeable backsheet 26 where the backsheet 26 is of a single-layer construction) can be a printed 19 gsm Berry Plastics XP-8695H film or equivalent commercially available from Berry Plastics Corporation, Evansville, Ind., U.S.A.

Where the backsheet 26 is of a single layer construction, it can be embossed and/or matte finished to provide a more cloth-like texture or appearance. The backsheet 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer and the liquid loading imparted by the intended use of the absorbent article 10. Additionally, the size and the absorbent capacity of the absorbent body 34 can be varied to accommodate wearers ranging from infants to adults.

The absorbent body 34 may have a length ranging from about 150, 160, 170, 180, 190, 200, 210, 220, 225, 230, 240, 250, 260, 270, 280, 290, 300, 310, 320, 330, 340, or 350 mm to about 355, 360, 380, 385, 390, 395, 400, 410, 415, 420, 425, 440, 450, 460, 480, 500, 510, or 520 mm. The absorbent body 34 may have a crotch region 16 width ranging from about 30, 40, 50, 55, 60, 65, or 70 mm to about 75, 80, 85, 90, 95, 100, 105, 110, 115, 120, 125, 130, 140, 150, 160, 170 or 180 mm. The width of the absorbent body 34 located within the front waist region 12 and/or the back waist region 14 of the absorbent article 10 may range from about 50, 55, 60, 65, 70, 75, 80, 85, 90, or 95 mm to about 100, 105, 110, 115, 120, 125 or 130 mm. As noted herein, the absorbent body 34 can have a length and width that can be less than or equal to the length and width of the absorbent article 10.

In an embodiment, the absorbent article 10 can be a diaper having the following ranges of lengths and widths of an absorbent body 34 having an hourglass shape: the length of the absorbent body 34 may range from about 170, 180, 190, 200, 210, 220, 225, 240 or 250 mm to about 260, 280, 300, 310, 320, 330, 340, 350, 355, 360, 380, 385, or 390 mm; the width of the absorbent body 34 in the crotch region 16 may range from about 40, 50, 55, or 60 mm to about 65, 70, 75, or 80 mm; the width of the absorbent body 34 in the front waist region 12 and/or the back waist region 14 may range from about 80, 85, 90, or 95 mm to about 100, 105, or 110 mm.

In an embodiment, the absorbent article 10 may be a training pant or youth pant having the following ranges of lengths and widths of an absorbent body 34 having an hourglass shape: the length of the absorbent body 34 may range from about 400, 410, 420, 440 or 450 mm to about 460, 480, 500, 510 or 520 mm; the width of the absorbent body 34 in the crotch region 16 may range from about 50, 55, or 60 mm to about 65, 70, 75, or 80 mm; the width of the absorbent body 34 in the front waist region 12 and/or the back waist region 14 may range from about 80, 85, 90, or 95 mm to about 100, 105, 110, 115, 120, 125, or 130 mm.

In an embodiment, the absorbent article 10 can be an adult incontinence garment having the following ranges of lengths and widths of an absorbent body 34 having a rectangular shape: the length of the absorbent body 34 may range from about 400, 410 or 415 to about 425 or 450 mm; the width of the absorbent body 34 in the crotch region 16 may range from about 90, or 95 mm to about 100, 105, or 110 mm. It should be noted that the absorbent body 34 of an adult incontinence garment may or may not extend into either or both the front waist region 12 or the back waist region 14 of the absorbent article 10.

The absorbent body 34 can have two surfaces such as a wearer facing surface 78 and a garment facing surface 80. Edges, such as longitudinal side edges, 36 and 38, and such as front and back end edges, 40 and 42, can connect the two surfaces, 78 and 80.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material.

In an embodiment, the absorbent body 34 may be constructed of a single layer of materials, or in the alternative, may be constructed of two or more layers of materials. In an embodiment in which the absorbent body 34 has two layers, the absorbent body 34 can have a wearer facing layer suitably composed of hydrophilic fibers and a garment facing layer suitably composed at least in part of a high absorbency material commonly known as superabsorbent material. In such an embodiment, the wearer facing layer of the absorbent body 34 can be suitably composed of cellulosic fluff, such as wood pulp fluff, and the garment facing layer of the absorbent body 34 can be suitably composed of superabsorbent material, or a mixture of cellulosic fluff and superabsorbent material. As a result, the wearer facing layer can have a lower absorbent capacity per unit weight than the garment facing layer. The wearer facing layer may alternatively be composed of a mixture of hydrophilic fibers and superabsorbent material, as long as the concentration of superabsorbent material present in the wearer facing layer is lower than the concentration of superabsorbent material present in the garment facing layer so that the wearer facing layer can have a lower absorbent capacity per unit weight than the garment facing layer. It is also contemplated that, in an embodiment, the garment facing layer may be composed solely of superabsorbent material without departing from the scope of this disclosure. It is also contemplated that, in an embodiment, each of the layers, the wearer facing and garment facing layers, can have a superabsorbent material such that the absorbent capacities of the two superabsorbent materials can be different and can provide the absorbent body 34 with a lower absorbent capacity in the wearer facing layer than in the garment facing layer.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber.

For example, one suitable type of fiber is a wood pulp that is a bleached, highly absorbent sulfate wood pulp containing primarily soft wood fibers. However, the wood pulp can be exchanged with other fiber materials, such as synthetic, polymeric, or meltblown fibers or with a combination of meltblown and natural fibers. In an embodiment, the cellulosic fluff can include a blend of wood pulp fluff. An example of wood pulp fluff can be "CoosAbsorb™ S Fluff Pulp" or equivalent available from Abitibi Bowater, Greenville, S.C., U.S.A., which is a bleached, highly absorbent sulfate wood pulp containing primarily southern soft wood fibers.

The absorbent body 34 can be formed with a dry-forming technique, an air-forming technique, a wet-forming technique, a foam-forming technique, or the like, as well as combinations thereof. A coform nonwoven material may also be employed. Methods and apparatus for carrying out such techniques are well known in the art.

Suitable superabsorbent materials can be selected from natural, synthetic, and modified natural polymers and materials. The superabsorbent materials can be inorganic materials, such as silica gels, or organic compounds, such as cross-linked polymers. Cross-linking may be covalent, ionic, Van der Waals, or hydrogen bonding. Typically, a superabsorbent material can be capable of absorbing at least about ten times its weight in liquid. In an embodiment, the superabsorbent material can absorb more than twenty-four times its weight in liquid. Examples of superabsorbent materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone, and the like. Additional polymers suitable for superabsorbent material include hydrolyzed, acrylonitrile grafted starch, acrylic acid grafted starch, polyacrylates and isobutylene maleic anhydride copolymers and mixtures thereof. The superabsorbent material may be in the form of discrete particles. The discrete particles can be of any desired shape, for example, spiral or semi-spiral, cubic, rod-like, polyhedral, etc. Shapes having a largest greatest dimension/smallest dimension ratio, such as needles, flakes, and fibers are also contemplated for use herein. Conglomerates of particles of superabsorbent materials may also be used in the absorbent body 34.

In an embodiment, the absorbent body 34 can be free of superabsorbent material. In an embodiment, the absorbent body 34 can have at least about 15% by weight of a superabsorbent material. In an embodiment, the absorbent body 34 can have at least about 15, 20, 25, 30, 35, 40, 45, 50, 55, 60, 65, 70, 75, 80, 85, 90, 95, 99 or 100% by weight of a superabsorbent material. In an embodiment, the absorbent body 34 can have less than about 100, 99, 95, 90, 85, 80, 75, 70, 65, 60, 55, 50, 45, 40, 35, 30, 25, or 20% by weight of a superabsorbent material. In an embodiment, the absorbent body 34 can have from about 15, 20, 25, 30, 35, 40, 45, 50, 55 or 60% to about 65, 70, 75, 80, 85, 90, 95, 99 or 100% by weight of a superabsorbent material. Examples of superabsorbent material include, but are not limited to, FAVOR SXM-9300 or equivalent available from Evonik Industries, Greensboro, N.C., U.S.A. and HYSORB 8760 or equivalent available from BASF Corporation, Charlotte, N.C., U.S.A.

The absorbent body 34 can be superposed over the inner layer 76 of the backsheet 26, extending laterally between the leg elastic members, 56 and 58, and can be bonded to the inner layer 76 of the backsheet 26, such as by being bonded thereto with adhesive. However, it is to be understood that the absorbent body 34 may be in contact with, and not bonded with, the backsheet 26 and remain within the scope of this disclosure.

In an embodiment, the backsheet 26 can be composed of a single layer and the absorbent body 34 can be in contact with the singer layer of the backsheet 26. In an embodiment, a layer, such as but not limited to, a fluid transfer layer 132, can be positioned between the absorbent body 40 and the backsheet 26.

Fluid Transfer Layer:

In various embodiments an absorbent article 10 can be constructed without a fluid transfer layer 132. In various embodiments the absorbent article 10 can have a fluid transfer layer 132. In an embodiment, the fluid transfer layer 132 can be in contact with the absorbent body 34. In an embodiment, the fluid transfer layer 132 can be bonded to the absorbent body 34. Bonding of the fluid transfer layer 132 to the absorbent body 34 can occur via any means known to one of ordinary skill, such as, but not limited to, adhesives. In an embodiment, a fluid transfer layer 132 can be positioned between the body facing liner 28 and the absorbent body 34. In an embodiment, a fluid transfer layer 132 can completely encompass the absorbent body 34 and can be sealed to itself. In such an embodiment, the fluid transfer layer 132 may be folded over on itself and then sealed using, for example, heat and/or pressure. In an embodiment a fluid transfer layer 132 may be composed of separate sheets of material which can be utilized to partially or fully encompass the absorbent body 34 and which can be sealed together using a sealing means such as an ultrasonic bonder or other thermochemical bonding means or the use of an adhesive.

In an embodiment, the fluid transfer layer 132 can be in contact with and/or bonded with the wearer facing surface 78 of the absorbent body 34. In an embodiment, the fluid transfer layer 132 can be in contact with and/or bonded with the wearer facing surface and at least one of the edges, 36, 38, 40, and/or 42, of the absorbent body 34. In an embodiment, the fluid transfer layer 132 can be in contact with and/or bonded with the wearer facing surface 78, at least one of the edges, 36, 38, 40, and/or 42, and the garment facing surface 80 of the absorbent body 34. In an embodiment, the absorbent body 34 may be partially or completely encompassed by a fluid transfer layer 132.

The fluid transfer layer 132 can be pliable, less hydrophilic than the absorbent body 34, and sufficiently porous to thereby permit liquid body exudates to penetrate through the fluid transfer layer 132 to reach the absorbent body 34. In an embodiment, the fluid transfer layer 132 can have sufficient structural integrity to withstand wetting thereof and of the absorbent body 34. In an embodiment, the fluid transfer layer 132 can be constructed from a single layer of material or it may be a laminate constructed from two or more layers of material.

In an embodiment, the fluid transfer layer 132 can include, but is not limited to, natural and synthetic fibers such as, but not limited to, polyester, polypropylene, acetate, nylon, polymeric materials, cellulosic materials such as wood pulp, cotton, rayon, viscose, LYOCELL® such as from Lenzing Company of Austria, or mixtures of these or other cellulosic fibers, and combinations thereof. Natural fibers can include, but are not limited to, wool, cotton, flax, hemp, and wood pulp. Wood pulps can include, but are not limited to, standard softwood fluffing grade such as "CoosAbsorb™ S Fluff Pulp" or equivalent available from Abitibi Bowater, Greenville, S.C., U.S.A., which is a bleached, highly absorbent sulfate wood pulp containing primarily southern soft wood fibers.

In various embodiments, the fluid transfer layer 132 can include cellulosic material. In various embodiments, the fluid transfer layer 132 can be creped wadding or a high-strength tissue. In various embodiments, the fluid transfer layer 132 can include polymeric material. In an embodiment, a fluid transfer layer 132 can include a spunbond material. In an embodiment, a fluid transfer layer 132 can include a meltblown material. In an embodiment, the fluid transfer layer 132 can be a laminate of a meltblown nonwoven material having fine fibers laminated to at least one spunbond nonwoven material layer having coarse fibers. In such an embodiment, the fluid transfer layer 132 can be a spunbond-meltblown ("SM") material. In an embodiment, the fluid transfer layer 132 can be a spunbond-meltblown-spunbond ("SMS") material. A non-limiting example of such a fluid transfer layer 132 can be a 10 gsm spunbond-meltblown-spunbond material. In various embodiments, the fluid transfer layer 132 can be composed of at least one material which has been hydraulically entangled into a nonwoven substrate. In various embodiments, the fluid transfer layer 132 can be composed of at least two materials which have been hydraulically entangled into a nonwoven substrate. In various embodiments, the fluid transfer layer 132 can have at least three materials which have been hydraulically entangled into a nonwoven substrate. A non-limiting example of a fluid transfer layer 132 can be a 33 gsm hydraulically entangled substrate. In such an example, the fluid transfer layer 132 can be a 33 gsm hydraulically entangled substrate composed of a 12 gsm spunbond material, a 10 gsm wood pulp material having a length from about 0.6 cm to about 5.5 cm, and an 11 gsm polyester staple fiber material. To manufacture the fluid transfer layer 132 just described, the 12 gsm spunbond material can provide a base layer while the 10 gsm wood pulp material and the 11 gsm polyester staple fiber material can be homogeneously mixed together and deposited onto the spunbond material and then hydraulically entangled with the spunbond material.

In various embodiments, a wet strength agent can be included in the fluid transfer layer 132. A non-limiting example of a wet strength agent can be Kymene 6500 (557LK) or equivalent available from Ashland Inc. of Ashland, Ky., U.S.A. In various embodiments, a surfactant can be included in the fluid transfer layer 132. In various embodiments, the fluid transfer layer 132 can be hydrophilic. In various embodiments, the fluid transfer layer 132 can be hydrophobic and can be treated in any manner known in the art to be made hydrophilic.

In an embodiment, the fluid transfer layer 132 can be in contact with and/or bonded with an absorbent body 34 which is made at least partially of particulate material such as superabsorbent material. In an embodiment in which the fluid transfer layer 132 at least partially or completely encompasses the absorbent body 34, the fluid transfer layer 132 should not unduly expand or stretch as this might cause the particulate material to escape from the absorbent body 34. In an embodiment, the fluid transfer layer 132, while in a dry state, should have respective extension values at peak load in the machine and cross directions of 30 percent or less and 40 percent or less, respectively.

In an embodiment, the fluid transfer layer 132 may have a longitudinal length the same as, greater than, or less than the longitudinal length of the absorbent body 34. The fluid transfer layer 132 can have a longitudinal length ranging from about 150, 160, 170, 180, 190, 200, 210, 220, 225, 230, 240, 250, 260, 270, 280, 290, 300, 310, 320, 330, 340, or 350 mm to about 355, 360, 380, 385, 390, 395, 400, 410, 415, 420, 425, 440, 450, 460, 480, 500, 510, or 520 mm.

Acquisition Layer:

In various embodiments the absorbent article 10 can have an acquisition layer 82. The acquisition layer 82 can help decelerate and diffuse surges or gushes of liquid body exudates penetrating the body facing liner 28. In an embodiment, the acquisition layer 82 can be positioned between the body facing liner 28 and the absorbent body 34 to take in and distribute body exudates for absorption by the absorbent body 34. In an embodiment, the acquisition layer 82 can be positioned between the body facing liner 28 and a fluid transfer layer 132 if a fluid transfer layer 132 is present.

In an embodiment, the acquisition layer 82 can be in contact with and/or bonded with the body facing liner 28. In an embodiment in which the acquisition layer 82 is bonded with the body facing liner 28, bonding of the acquisition layer 82 to the body facing liner 28 can occur through the use of an adhesive and/or point fusion bonding. The point fusion bonding can be selected from, but is not limited to, ultrasonic bonding, pressure bonding, thermal bonding, and combinations thereof. In an embodiment, the point fusion bonding can be provided in any pattern as deemed suitable.

The acquisition layer 82 may have any longitudinal length dimension as deemed suitable. The acquisition layer 82 may have a longitudinal length from about 120, 130, 140, 150, 160, 170, 180, 190, 200, 210, 220, 225, 230, 240, or 250 mm to about 260, 270, 280, 290, 300, 310, 320, 340, 350, 360, 380, 400, 410, 415, 420, 425, 440, 450, 460, 480, 500, 510 or 520 mm. In an embodiment, the acquisition layer 82 can have any length such that the acquisition layer 82 can be coterminous with the waist edges, 22 and 24, of the absorbent article 10.

In an embodiment, the longitudinal length of the acquisition layer 82 can be the same as the longitudinal length of the absorbent body 34. In such an embodiment the midpoint of the longitudinal length of the acquisition layer 82 can substantially align with the midpoint of the longitudinal length of the absorbent body 34.

In an embodiment, the longitudinal length of the acquisition layer 82 can be shorter than the longitudinal length of the absorbent body 34. In such an embodiment, the acquisition layer 82 may be positioned at any desired location along the longitudinal length of the absorbent body 34. As an example of such an embodiment, the absorbent article 10 may contain a target area where repeated liquid surges typically occur in the absorbent article 10. The particular location of a target area can vary depending on the age and gender of the wearer of the absorbent article 10. For example, males tend to urinate further toward the front region of the absorbent article 10 and the target area may be phased forward within the absorbent article 10. For example, the target area for a male wearer may be positioned about 2¾" forward of the longitudinal midpoint of the absorbent body 34 and may have a length of about ±3" and a width of about ±2". The female target area can be located closer to the center of the crotch region 16 of the absorbent article 10. For example, the target area for a female wearer may be positioned about 1" forward of the longitudinal midpoint of the absorbent body 34 and may have a length of about ±3" and a width of about ±2". As a result, the relative longitudinal placement of the acquisition layer 82 within the absorbent article 10 can be selected to best correspond with the target area of either or both categories of wearers.

In an embodiment, the absorbent article 10 may contain a target area centered within the crotch region 16 of the absorbent article 10 with the premise that the absorbent article 10 would be worn by a female wearer. The acquisition layer 82, therefore, may be positioned along the longitudinal length of the absorbent article 10 such that the acquisition layer 82 can be substantially aligned with the target area of the absorbent article 10 intended for a female wearer. Alternatively, the absorbent article 10 may contain a target area positioned between the crotch region 16 and the front waist region 12 of the absorbent article 10 with the premise that the absorbent article 10 would be worn by a male wearer. The acquisition layer 82, therefore, may be positioned along the longitudinal length of the absorbent article 10 such that the acquisition layer 82 can be substantially aligned with the target area of the absorbent article 10 intended for a male wearer.

In an embodiment, the acquisition layer 82 can have a size dimension that is the same size dimension as the target area of the absorbent article 10 or a size dimension greater than the size dimension of the target area of the absorbent article 10. In an embodiment, the acquisition layer 82 can be in contact with and/or bonded with the body facing liner 28 at least partially in the target area of the absorbent article 10.

In various embodiments, the acquisition layer 82 can have a longitudinal length shorter than, the same as, or longer than the longitudinal length of the absorbent body 34. In an embodiment in which the absorbent article 10 is a diaper, the acquisition layer 82 may have a longitudinal length from about 120, 130, 140, 150, 160, 170, or 180 mm to about 200, 210, 220, 225, 240, 260, 280, 300, 310 or 320 mm. In such an embodiment, the acquisition layer 82 may be shorter in longitudinal length than the longitudinal length of the absorbent body 34 and may be phased from the front end edge 40 of the absorbent body 34 a distance of from about 15, 20, or 25 mm to about 30, 35 or 40 mm. In an embodiment in which the absorbent article 10 may be a training pant or youth pant, the acquisition layer 82 may have a longitudinal length from about 120, 130, 140, 150, 200, 210, 220, 230, 240 or 250 mm to about 260, 270, 280, 290, 300, 340, 360, 400, 410, 420, 440, 450, 460, 480, 500, 510 or 520 mm. In such an embodiment, the acquisition layer 82 may have a longitudinal length shorter than the longitudinal length of the absorbent body 34 and may be phased a distance of from about 25, 30, 35 or 40 mm to about 45, 50, 55, 60, 65, 70, 75, 80 or 85 mm from the front end edge 40 of the absorbent body 34. In an embodiment in which the absorbent article 10 is an adult incontinence garment, the acquisition layer 82 may have a longitudinal length from about 200, 210, 220, 230, 240, or 250 mm to about 260, 270, 280, 290, 300, 320, 340, 360, 380, 400, 410, 415, 425, or 450 mm. In such an embodiment, the acquisition layer 82 may have a longitudinal length shorter than the longitudinal length of the absorbent body 34 and the acquisition layer 82 may be phased a distance of from about 20, 25, 30 or 35 mm to about 40, 45, 50, 55, 60, 65, 70 or 75 mm from the front end edge 40 of the absorbent body 34.

The acquisition layer 82 may have any width as desired. The acquisition layer 82 may have a width dimension from about 15, 20, 25, 30, 35, 40, 45, 50, 55, 60, or 70 mm to about 80, 90, 100, 110, 115, 120, 130, 140, 150, 160, 170, or 180 mm. The width of the acquisition layer 82 may vary dependent upon the size and shape of the absorbent article 10 within which the acquisition layer 82 will be placed. The acquisition layer 82 can have a width smaller than, the same as, or larger than the width of the absorbent body 34. Within the crotch region 16 of the absorbent article 10, the acquisition layer 82 can have a width smaller than, the same as, or larger than the width of the absorbent body 34.

In an embodiment, the acquisition layer 82 can include natural fibers, synthetic fibers, superabsorbent material, woven material, nonwoven material, wet-laid fibrous webs, a substantially unbounded airlaid fibrous web, an operatively bonded, stabilized-airlaid fibrous web, or the like, as well as combinations thereof. In an embodiment, the acquisition layer 82 can be formed from a material that is substantially hydrophobic, such as a nonwoven web composed of polypropylene, polyethylene, polyester, and the like, and combinations thereof.

Body Facing Liner:

In various embodiments, the body facing liner 28 of the absorbent article 10 can overlay the absorbent body 34 and the backsheet 26 and can isolate the wearer's skin from liquid waste retained by the absorbent body 34. In various embodiments, a fluid transfer layer 132 can be positioned between the body facing liner 28 and the absorbent body 34. In various embodiments, an acquisition layer 82 can be positioned between the body facing liner 28 and the absorbent body 34 or a fluid transfer layer 132, if present. In various embodiments, the body facing liner 28 can be bonded to the acquisition layer 82, or the fluid transfer layer 132 if no acquisition layer 82 is present, via adhesive and/or by a point fusion bonding. The point fusion bonding may be selected from ultrasonic, thermal, pressure bonding, and combinations thereof.

In an embodiment, the body facing liner 28 can extend beyond the absorbent body 34 and/or a fluid transfer layer 132, and/or an acquisition layer 82 to overlay a portion of the backsheet 26 and can be bonded thereto by any method deemed suitable, such as, for example, by being bonded thereto by adhesive, to substantially enclose the absorbent body 34 between the backsheet 26 and the body facing liner 28. The body facing liner 28 may be narrower than the backsheet 26, but it is to be understood that the body facing liner 28 and the backsheet 26 may be of the same dimensions. It is also contemplated that the body facing liner 28 may not extend beyond the absorbent body 34 and/or may not be secured to the backsheet 26. The body facing liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The body facing liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the body facing liner 28. The body facing liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof.

For example, the body facing liner 28 can be composed of a meltblown or spunbond web of polyolefin fibers. Alternatively, the body facing liner 28 can be a bonded-carded web composed of natural and/or synthetic fibers. The body facing liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire body facing liner 28 or it can be selectively applied to particular sections of the body facing liner 28.

In an embodiment, a body facing liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a body facing liner 28 can be a spunbond substrate with a basis weight from about 10 or 12 to about 15 or 20 gsm. In an embodiment, a body facing liner 28 can be a 12 gsm spunbond-meltblown-spunbond substrate having 10% meltblown content applied between the two spunbond layers.

Although the backsheet 26 and body facing liner 28 can include elastomeric materials, it is contemplated that the backsheet 26 and the body facing liner 28 can be composed of materials which are generally non-elastomeric. In an embodiment, the body facing liner 28 can be stretchable, and more suitably elastic. In an embodiment, the body facing liner 28 can be suitably stretchable and more suitably elastic in at least the lateral or circumferential direction of the absorbent article 10. In other aspects, the body facing liner 28 can be stretchable, and more suitably elastic, in both the lateral and the longitudinal directions.

Containment Flaps:

In an embodiment, containment flaps, 44 and 46, can be secured to the body facing liner 28 of the absorbent article 10 in a generally parallel, spaced relation with each other laterally inward of the longitudinal side edges, 18 and 20, to provide a barrier against the flow of body exudates to the leg openings. In an embodiment, the containment flaps, 44 and 46, can extend longitudinally from the front waist region 12 of the absorbent article 10, through the crotch region 16 to the back waist region 14 of the absorbent article 10. The containment flaps, 44 and 46, can be bonded to the body facing liner 28 by a seam of adhesive to define a fixed proximal end 84 of the containment flaps, 44 and 46.

The containment flaps, 44 and 46, can be constructed of a fibrous material which can be similar to the material forming the body facing liner 28. Other conventional material, such as polymer films, can also be employed. Each containment flap, 44 and 46, can have a moveable distal end 86 which can include flap elastics, such as flap elastics 48 and 50, respectively. Suitable elastic materials for the flap elastic, 48 and 50, can include sheets, strands or ribbons of natural rubber, synthetic rubber, or thermoplastic elastomeric materials.

The flap elastics, 48 and 50, as illustrated, can have two strands of elastomeric material extending longitudinally along the distal ends 86 of the containment flaps, 44 and 46, in generally parallel, spaced relation with each other. The elastic strands can be within the containment flaps, 44 and 46, while in an elastically contractible condition such that contraction of the strands gathers and shortens the distal ends 86 of the containment flaps, 44 and 46. As a result, the elastic strands can bias the distal ends 86 of each containment flap, 44 and 46, toward a position spaced from the proximal end 84 of the containment flaps, 44 and 46, so that the containment flaps, 44 and 46, can extend away from the body facing liner 28 in a generally upright orientation of the containment flaps, 44 and 46, especially in the crotch region 16 of the absorbent article 10, when the absorbent article 10 is fitted on the wearer. The distal end 86 of the containment flaps, 44 and 46, can be connected to the flap elastics, 48 and 50, by partially doubling the containment flap, 44 and 46, material back upon itself by an amount which can be sufficient to enclose the flap elastics, 48 and 50. It is to be understood, however, that the containment flaps, 44 and 46, can have any number of strands of elastomeric material and may also be omitted from the absorbent article 10 without departing from the scope of this disclosure.

Leg Opening Adjustment Mechanisms:

The absorbent article 10 can have a pair of leg opening adjustment mechanisms 60 which can each be positioned laterally inward of each longitudinal side edge, 18 and 20, of the absorbent article 10 and which can be oriented in the longitudinal direction 30 of the absorbent article 10. In an embodiment, each leg opening adjustment mechanism 60 can be positioned laterally outward of the absorbent body 34 of the absorbent article 10. Each leg opening adjustment mechanism 60 can include an adjustment member 62 and a cover 68.

The leg opening adjustment mechanisms 60 can be positioned on either the body facing surface 70 or the garment facing surface 72 of the backsheet 26 as deemed suitable. As will be described in more detail herein, to position a leg opening adjustment mechanism 60 on the desired surface, 70 or 72, of the backsheet 26, the longitudinal direction edges 96 and at least one of the lateral direction edges 98 of the cover 68 of the leg opening adjustment mechanism 60 can be bonded to the desired surface, 70 or 72, of the backsheet 26 and the adjustment member 62 can be positioned in a pocket created between the cover 68 of the leg opening adjustment mechanism 60 and the desired surface, 70 or 72, of the backsheet 26. In an embodiment, such as illustrated in the non-limiting illustration of FIG. 1, the leg opening adjustment mechanism 60 can be positioned on the body facing surface 70 of the backsheet 26. In an embodiment, such as illustrated in the non-limiting illustration of FIG. 7, the leg opening adjustment mechanism 60 can be positioned on the garment facing surface 72 of the backsheet 26.

In an embodiment, the leg opening adjustment mechanisms 60 can be positioned at least partially in the crotch region 16 of the absorbent article 10. In an embodiment, the leg opening adjustment mechanisms 60 can be positioned entirely within the crotch region 16 of the absorbent article 10. In an embodiment, the leg opening adjustment mechanisms 60 can be positioned at least partially in the crotch region 16 and at least partially in at least one of the front waist region 12 and/or the back waist region 14 of an absorbent article 10. In an embodiment, the leg opening adjustment mechanisms 60 can be positioned in the crotch region 16 and at least partially in the front waist region 12 and at least partially in the back waist region 14 of an absorbent article 10.

In an embodiment, a cover 68 of a leg opening adjustment mechanism 60 can be positioned at least partially in the crotch region 16 of an absorbent article 10. In an embodiment, a cover 68 of a leg opening adjustment mechanism 60 can be positioned entirely within the crotch region 16 of an absorbent article 10. In an embodiment, a cover 68 of a leg opening adjustment mechanism 60 can be positioned at least partially in the crotch region 16 and at least partially in at least one of the front waist region 12 and/or the back waist region 14 of an absorbent article 10. In an embodiment, a cover 68 of a leg opening adjustment mechanism 60 can be positioned in the crotch region 16 and at least partially in the front waist region 12 and at least partially in the back waist region 14 of an absorbent article 10.

The cover 68 of a leg opening adjustment mechanism 60 can have any length in the longitudinal direction 30 as deemed suitable. In an embodiment, the cover 68 of a leg opening adjustment mechanism 60 can have a length in the longitudinal direction 30 from about 30, 40, 50, 55, 60, 65, 70, 75, 80, 85, 90, 95, 100, 110, 120, 130, 140, 150, 160, 170, 180, 190, 200, 210, 220, 225, 230, 240, 250, 260, 270, 280, 290, 300, 310, 320, 330, 340 or 350 mm to about 355, 360, 380, 385, 390, 395, 400, 410, 415, 420, 425, 440, 450, 460, 480, 500, 510, or 520 mm. In an embodiment, the cover 68 of a leg opening adjustment mechanism 60 can have any width in the transverse direction 32 as deemed suitable. In an embodiment, the cover 68 of the leg opening adjustment mechanism 60 can have a width in the transverse direction 32 from about 5, 10, 15 or 20 mm to about 25, 30, 35 or 40 mm.

The cover 68 of a leg opening adjustment mechanism 60 can be substantially rectilinear in shape and can have two opposed longitudinal direction edges 96 and two opposed lateral direction edges 98. In an embodiment, both of the longitudinal direction edges 96 and at least one of the lateral direction edges 98 of a cover 68 of a leg opening adjustment mechanism 60 can be bonded to the desired surface, 70 or 72, of the backsheet 26. In such an embodiment, the lateral direction edge 98 which can be bonded to the desired surface, 70 or 72, of the backsheet 26 can be either the lateral direction edge 98 closest in proximity to the front waist edge 22 of the absorbent article 10 or the lateral direction edge 98 closest in proximity to the back waist edge 24 of the absorbent article 10. In an embodiment, both of the longitudinal direction edges 96 of a cover 68 and the lateral direction edge 98 of the cover 68 which is closest in proximity to the front waist edge 22 of the absorbent article 10 can be bonded to the desired surface, 70 or 72, of the backsheet 26. In an embodiment, both of the longitudinal direction edges 96 of a cover 68 and the lateral direction edge 98 of the cover 68 which is closest in proximity to the back waist edge 24 of the absorbent article 10 can be bonded to the desired surface, 70 or 72, of the backsheet 26. The bonding of the two longitudinal direction edges 96 of a cover 68 and at least one of the lateral direction edges 98 of the cover 68 can create a pocket between the cover 68 of a leg opening adjustment mechanism 60 and the desired surface, 70 or 72, of the backsheet 26. In an embodiment, both longitudinal direction edges 96 and both lateral direction edges 98 of a cover 68 can be bonded to a desired surface, 70 or 72, of the backsheet 26. The bonding of both longitudinal direction edges 96 and both lateral direction edges 98 can create a pocket between the cover 68 of a leg opening adjustment mechanism 60 and the desired surface, 70 or 72, of the backsheet 26.

Figure 7:
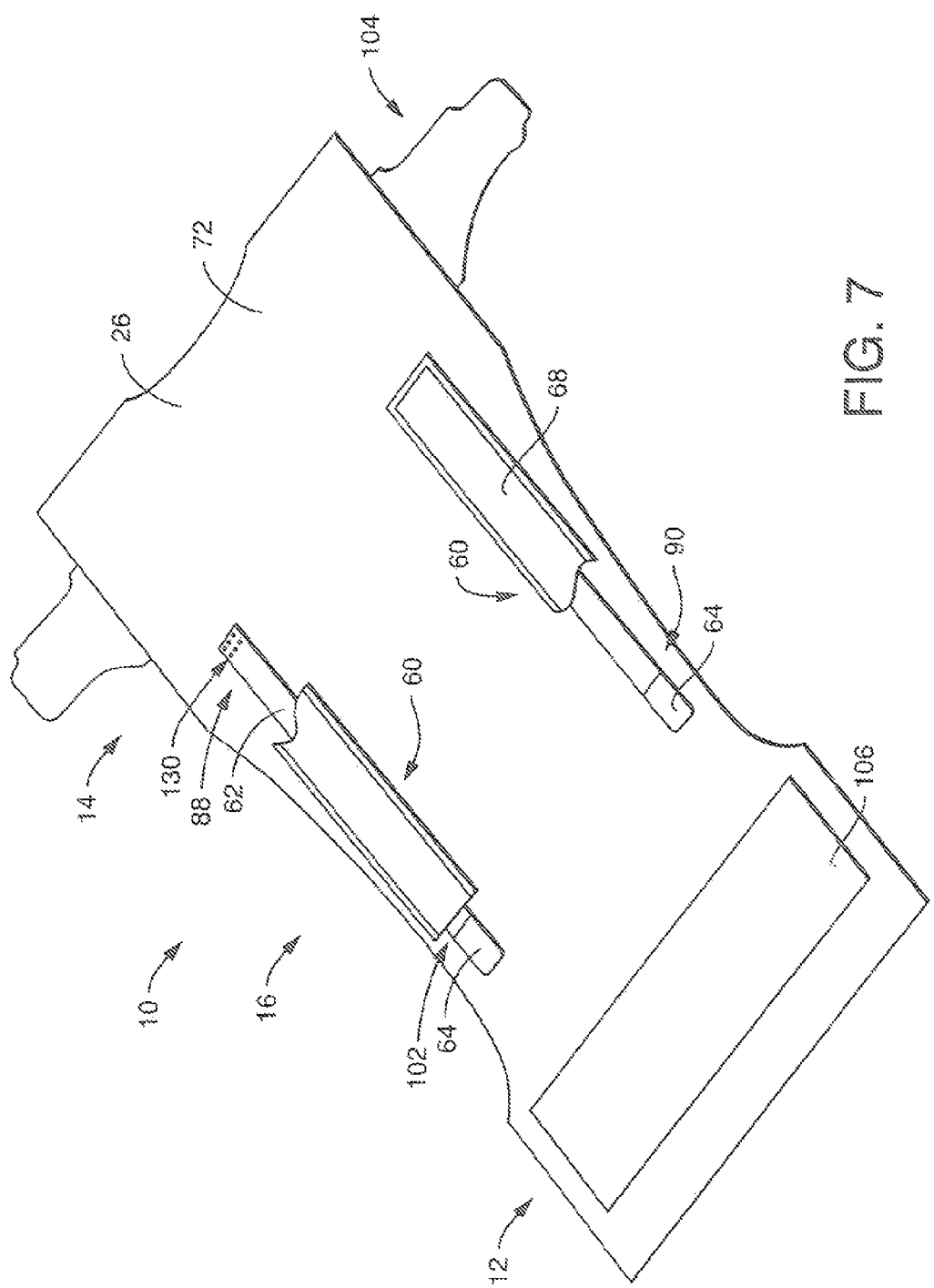
FIG. 7 is a plan view of a non-limiting illustration of an absorbent article, such as, for example, a diaper, in an unfastened, stretched and laid flat condition with the surface of the absorbent article which contacts the wearer's clothing facing the viewer and with portions cut away for clarity of illustration.

In an embodiment such as when a cover 68 of a leg opening adjustment mechanism 60 can be bonded to the garment facing surface 72 of the backsheet 26, at least one of the lateral direction edges 98 of the cover 68 can remain unbonded and can create an opening 102 wherein the cover 68 of the leg opening adjustment mechanism 60 is not bonded to the garment facing surface 72 of the backsheet 26 (illustrated in FIG. 7). In such an embodiment, the adjustment member 62 can be positioned within the pocket existing between the cover 68 and the garment facing surface 72 of the backsheet 26 and can extend outside of the pocket by passing through the opening 102 created by the unbonded lateral direction edge 98 (illustrated in FIG. 7). In an embodiment such as when a cover 68 of a leg opening adjustment mechanism 60 can be bonded to the body facing surface 70 of the backsheet, both longitudinal direction edges 96 and both lateral direction edges 98 can be bonded to the body facing surface 70 of the backsheet 26 (illustrated in FIG. 1). In such an embodiment, the adjustment member 62 can be fully enclosed within a pocket existing between the cover 68 of the leg opening adjustment mechanism 60 and the body facing surface 70 of the backsheet 26 (illustrated in FIG. 1). As will be described herein, in such an embodiment an opening 92 can be created in the backsheet 26 to allow the adjustment member 62 to be reachable by the user of the absorbent article 10.

The longitudinal direction edges 96 and at least one, or both, lateral direction edges 98 of the cover 68 of a leg opening adjustment mechanism 60 can be bonded to a desired surface, 70 or 72, of the backsheet 26 by any method deemed suitable such as, but not limited to, adhesives, cohesives, mechanical bonds, pressure bonds, ultrasonic bonds, and thermal bonds. In an embodiment, such as, for example, when the leg opening adjustment mechanism 60 can be positioned on the body facing surface 70 of the backsheet 26, each of the longitudinal direction edges 96 and each of the lateral direction edges 98 of the cover 68 of a leg opening adjustment mechanism 60 can be bonded to the body facing surface 70 of the backsheet 26 with a leak-proof bond.

In an embodiment, the cover 68 of a leg opening adjustment mechanism 60 can be constructed of materials which can be compatible with the body facing surface 70 or the garment facing surface 72 of the backsheet 26. In an embodiment, the cover 68 of a leg opening adjustment mechanism 60 can be constructed of material which can be the same as the material of the body facing surface 70 or the garment facing surface 72 of the backsheet 26. In an embodiment, the cover 68 can be breathable and/or liquid impermeable. In an embodiment, the cover 68 can be elastic, stretchable or non-stretchable. In an embodiment, the cover 68 of a leg opening adjustment mechanism 60 can be constructed of a single layer, multiple layers, laminates, spunbond fabrics, films, polyethylene films, polypropylene films, nylon films, meltblown fabrics, elastic netting, microporous webs, bonded-carded webs or foams provided by elastomeric or polymeric materials, nonwovens, polypropylene, polyethylene, and any other known fiber and/or synthetic materials, and combinations thereof. In an embodiment, the cover 68 can be constructed of a microporous polymeric film such as polyethylene, polypropylene, nylon, and combinations thereof. In an embodiment, the cover 68 of the leg opening adjustment mechanism 60 can be constructed of any material capable of providing a moisture barrier. In an embodiment, the cover 68 of a leg opening adjustment mechanism 60 can be constructed of any material having a low coefficient of friction to allow for movement of an adjustment member 62 between the cover 68 and the desired surface, 70 or 72, of the backsheet 26. In an embodiment, the cover 68 of a leg opening adjustment mechanism 60 can be constructed from any material such as described herein for constructing the outer cover 26. In an embodiment, such as, for example, when the leg opening adjustment mechanism 60 is positioned on the body facing surface 70 of the backsheet 26, the cover 68 of a leg opening adjustment mechanism 60 can be constructed of a liquid impermeable material. In an embodiment, the cover 68 of a leg opening adjustment mechanism 60 can be constructed from a printed 19 gsm Berry Plastics XP-8695H film or equivalent commercially available from Berry Plastics Corporation, Evansville, Ind., U.S.A.

As illustrated in FIGS. 1 and 7, an adjustment member 62 can be positioned between a cover 68 of a leg opening adjustment mechanism 60 and the body facing surface 70 of the backsheet 26 or the garment facing surface 72 of the backsheet 26, respectively. The adjustment member 62, which can be positioned between the cover 68 of a leg opening adjustment mechanism 60 and the desired surface, 70 or 72, of the backsheet 26, can have two ends, a first end 88 and a second end 90. The first end 88 can be permanently bonded, in a bonding area 130, to the desired surface, 70 or 72, of the backsheet 26 of the absorbent article 10 or can be permanently bonded to the cover 68 of the leg opening adjustment mechanism 60. The bonding of the first end 88 of the adjustment member 62 to the desired surface, 70 or 72, of the backsheet 26 or to the cover 68 of the leg opening adjustment mechanism 60, in a bonding area 130, can occur by any method deemed suitable such as, for example, adhesives, cohesives, mechanical bonds, pressure bonds, thermal bonds, and ultrasonic bonds. From bonding area 130 at the first end 88 of the adjustment member 62, the adjustment member 62 can remain substantially unbonded throughout the pocket created between the cover 68 of the leg opening adjustment mechanism 60 and the desired surface, 70 or 72, of the backsheet 26. In an embodiment, except for the bonding of the adjustment member 62 in the bonding area 130 at the first end 88, the adjustment member 62 is not bonded in any other location within the pocket and is, therefore, free to move within the confines of the pocket created between the cover 68 of the leg opening adjustment mechanism 60 and the surface, 70 or 72, of the backsheet 26. In such an embodiment, except for the bonding of the adjustment member 62 in the bonding area 130 at the first end 88, the adjustment member 62 can also move freely external to the pocket created between the cover 68 of the leg opening adjustment mechanism 60 and the desired surface, 70 or 72, of the backsheet 26. The ability of the adjustment member 62 to move freely is important to allow for uniform tension to be provided when the adjustment member 62 is engaged by the user of the absorbent article 10. Without being bound by theory, it is believed that uniform tension can provide proper fit of the absorbent article 10 around the leg openings and in the crotch region 16 of the absorbent article 10. Without being bound by theory, it is believed that uneven tension can result in uneven or improper fit of the absorbent article 10 about the legs of the wearer of the absorbent article 10.

The adjustment member 62 can be constructed from elastic and/or inelastic materials. Such materials can include, but are not limited to, rubber elastics, synthetic rubber elastics, elastomeric foams, elastic films, nonwovens, polyethylenes, polypropylenes, laminates, foams, nonwovens, string, twine, and rope. The adjustment member 62 can include elastic materials such as, but not limited to, sheets, strands or ribbons of natural rubber, synthetic rubber, or thermoplastic elastomeric polymer materials. In an embodiment, the adjustment member 62 can have 1, 2, 3, 4, 5, or 6 strands of elastic material. In an embodiment, the adjustment member 62 can have a carrier web and an elastic material attached to the carrier web using an adhesive such as a construction adhesive. In such an embodiment, an example of a carrier material is a "NW SMS 17 gsm Multi-Color Nonwettable Wire Weave" available from the Kimberly-Clark Corporation, USA. In such an embodiment, an example of an elastic material is "Radici S17 800 dtex Direct Spun" available from Radici Spandex Corporation, USA. In such an embodiment, an example of a construction adhesive is "Bostik-H20030 Hot Melt Adhesive" available from Bostik Incorporated, USA. In an embodiment, the adjustment member 62 can be a laminate made of two facings of "NW SMS 17 gsm Multi-Color Nonwettable Wire Weave" carrier material available from the Kimberly-Clark Corporation, USA covering 3 strands of a "Radici S17 800 dtex Direct Spun" elastic material available from Radici Spandex Corporation, USA. The elastic strands are adhesively held with a construction adhesive "Bostik-H20030 Hot Melt Adhesive" available from Bostik Incorporated, USA. The width of the final laminate is about 18 mm.

The adjustment member 62 can have any length and width as deemed suitable to provide the desired tension and closure about the legs of a wearer of an absorbent article 10. In an embodiment, the adjustment member can have a length which can be shorter than, longer than, or the same size as the cover 68 of the leg opening adjustment mechanism 60. In an embodiment, the adjustment member 62 can have a width which can be smaller than the width of the cover 68 of the leg opening adjustment mechanism 60. In an embodiment, the adjustment member 62 can have a width from about 3, 5, 10 or 15 mm to about 18, 20, 25 or 30 mm.

The adjustment member 62 can have a second end 90, opposite to the first end 88, which is not permanently bonded to the absorbent article 10. The second end 90 of the adjustment member 62 can terminate in a grasping tab 64. The grasping tab 64 can be a location where a user of the absorbent article 10 can grasp the adjustment member 62 to engage the adjustment member 62 to adjust and provide the desired tension and closure of the absorbent article 10 about the legs of the wearer of the absorbent article 10. The grasping tab 64 can be constructed of the same material or a different material as the construction of the adjustment member 62. In an embodiment, the grasping tab 64 can be constructed from materials which can include, but are not limited to, rubber elastics, synthetic rubber elastics, elastomeric foams, elastic films, nonwovens, polyethylenes, polypropylenes, laminates, foams, nonwovens, string, twine, and rope. In an embodiment, the grasping tab 64 can be constructed from a nonwoven material, such as, for example, "NW SMS 57.6 gsm Multi-Color Nonwet Wire Weave" which is a 57.6 gsm white or blue, wire weave bonded, polypropylene SMS material available from Kimberly-Clark Corporation, USA.

Figure 2:
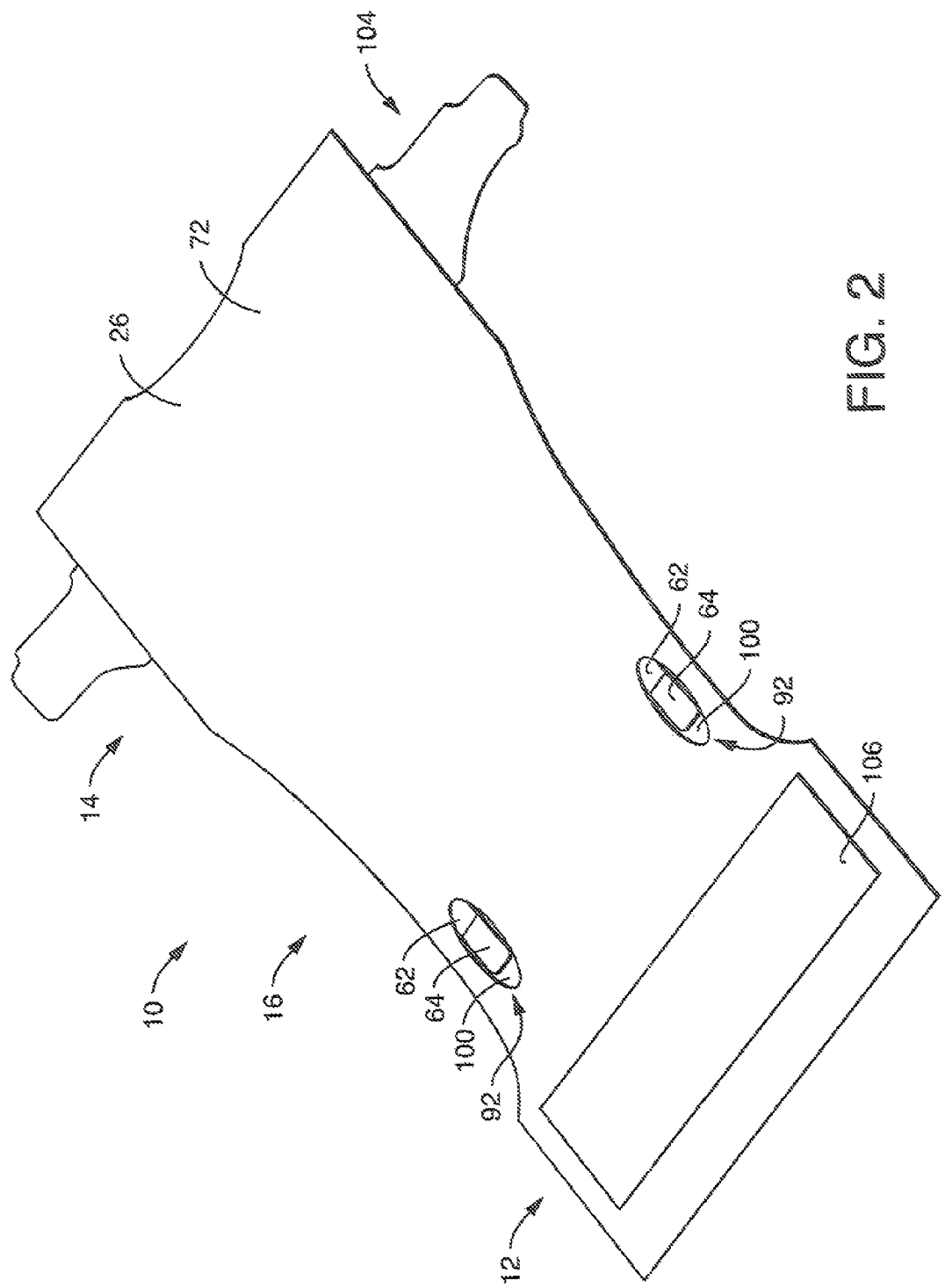
FIG. 2 is a plan view of a non-limiting illustration of the absorbent article of FIG. 1, in an unfastened, stretched and laid flat condition with the surface of the absorbent article which contacts the wearer's clothing facing the viewer.

As described herein, the adjustment member 62 can extend through an opening, either opening 92 in the backsheet 26 or opening 102. In an embodiment in which the leg opening adjustment mechanism 60 can be positioned on the body facing surface 70 of the backsheet 26, the backsheet 26 can be provided with an opening 92 in the vicinity of the grasping tab 64 of the adjustment member 62. The opening 92 can be in any location deemed suitable to provide access for a user to the grasping tab 64 and deemed suitable to not promote leakage of body exudates through the opening 92. In such an embodiment, the grasping tab 64 can be refastenably attached to the garment facing surface 100 of the cover 68 of the leg opening adjustment mechanism 60 which faces the opening 92 in the backsheet 26 (illustrated in FIG. 2) or the grasping tab 64 can be refastenably attached to a portion of the backsheet 26 located adjacent to the opening 92 in the backsheet 26. By refastenably attaching the grasping tab 64 to either a portion of the garment facing surface 100 of the cover 68 of the leg opening adjustment mechanism 60 facing the opening 92 or to a portion of the backsheet 26 adjacent the opening 92 in the backsheet, the grasping tab 64 can be within reach of a user of the absorbent article 10. The opening 92 in the backsheet 26 can be any size and shape deemed suitable to allow for the grasping tab 64 to be accessible by a user. In an embodiment, the opening 92 can have a shape such as a circle, oval, square, rectangle, triangle, diamond, trapezoid, rhombus, or any other shape deemed suitable. The opening 92 can have a size deemed suitable to allow for the passage of the grasping tab 64 and the adjustment member 62 through the opening 92 when a user has grasped the grasping tab 64 and has engaged the adjustment member 62 to adjust and provide the desired tension and closure of the leg openings about the legs of the wearer. As will be described herein, the grasping tab 64 can be provided with fasteners 66 which can prevent the adjustment member 62 and the grasping tab 64 from slipping back into the pocket and out of reach of a user. FIG. 2 is a plan view of a non-limiting illustration of the absorbent article of FIG. 1, in an unfastened, stretched and laid-flat condition with the garment facing surface 72 of the backsheet 26 facing the viewer. FIG. 2 provides a non-limiting illustration of an absorbent article 10 with a leg opening adjustment mechanism 60 positioned on the body facing surface 70 of the backsheet 26 in which the grasping tab 64 can be refastenably attached to a portion of the garment facing surface 100 of the cover 68 of the leg opening adjustment mechanism 60 facing the opening 92 in the backsheet 26. In the non-limiting embodiment illustrated in FIG. 2, the grasping tab 64 can be within reach of a user of the absorbent article 10.

In an embodiment in which the leg opening adjustment mechanism 60 can be positioned on the garment facing surface 72 of the backsheet 26, at least a portion of the grasping tab 64 can be refastenably attached to a portion of the garment facing surface 72 of the backsheet 26 located adjacent to the opening 102. By refastenably attaching the grasping tab 64 to a portion of the backsheet 26 adjacent the opening 102, the grasping tab 64 can be within reach of a user of the absorbent article 10. FIG. 7 is a plan view of a non-limiting illustration of an absorbent article in an unfastened, stretched and laid-flat condition with the garment facing surface 72 of the backsheet 26 facing the viewer. FIG. 7 provides a non-limiting illustration of an absorbent article 10 with a leg opening adjustment mechanism 60 positioned on the body facing surface 70 of the backsheet 26 in which the grasping tab 64 can be refastenably attached to a portion of the garment facing surface 72 of the backsheet 26. In the non-limiting embodiment illustrated in FIG. 7, the grasping tab 64 can be within reach of a user of the absorbent article 10.

Figure 3:
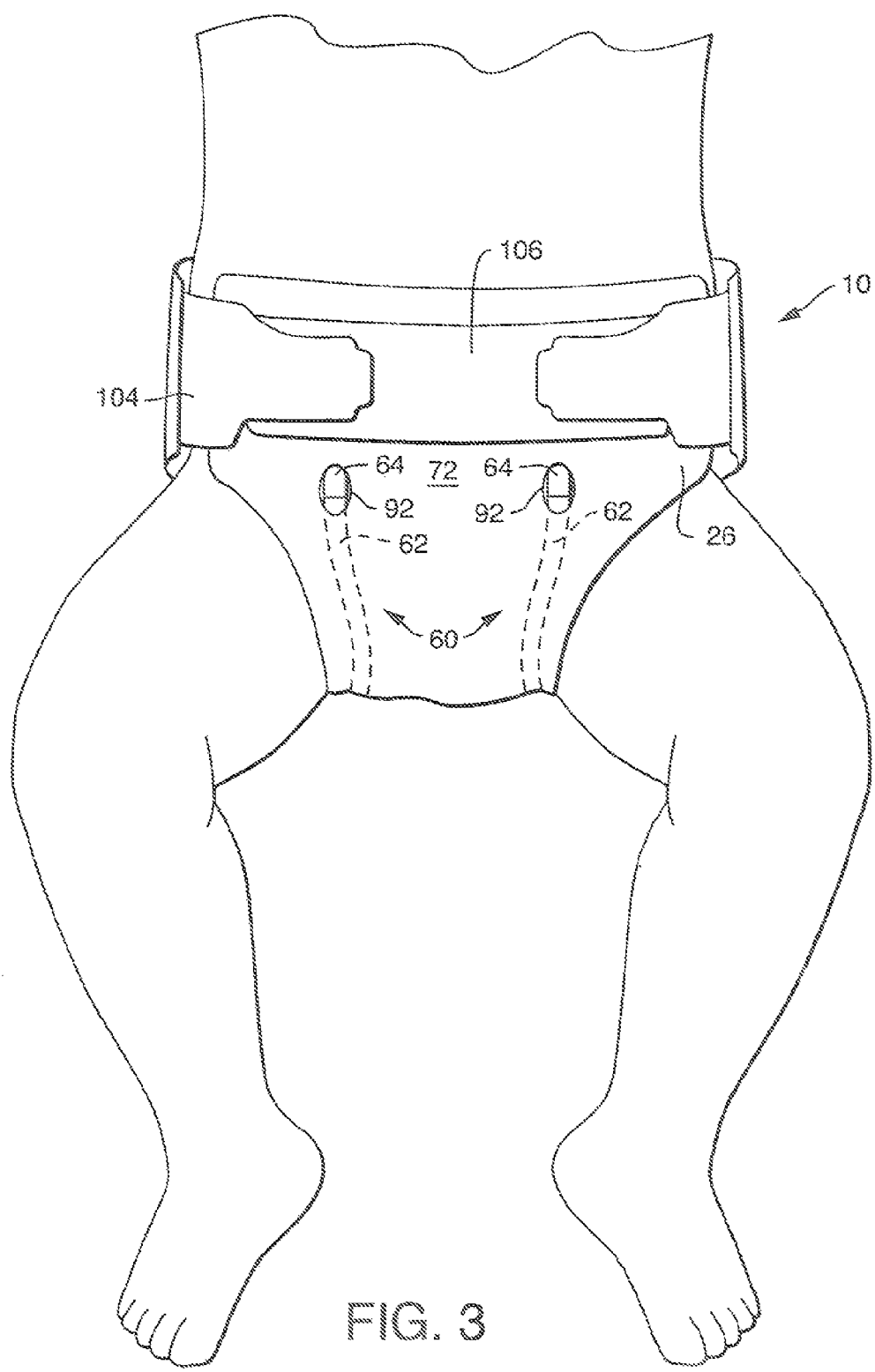
FIG. 3 is a front view of a non-limiting illustration of the absorbent article of FIG. 1, in which the waist fastening system is holding the absorbent article in a fastened condition about the lower torso of a wearer.
Figure 4:
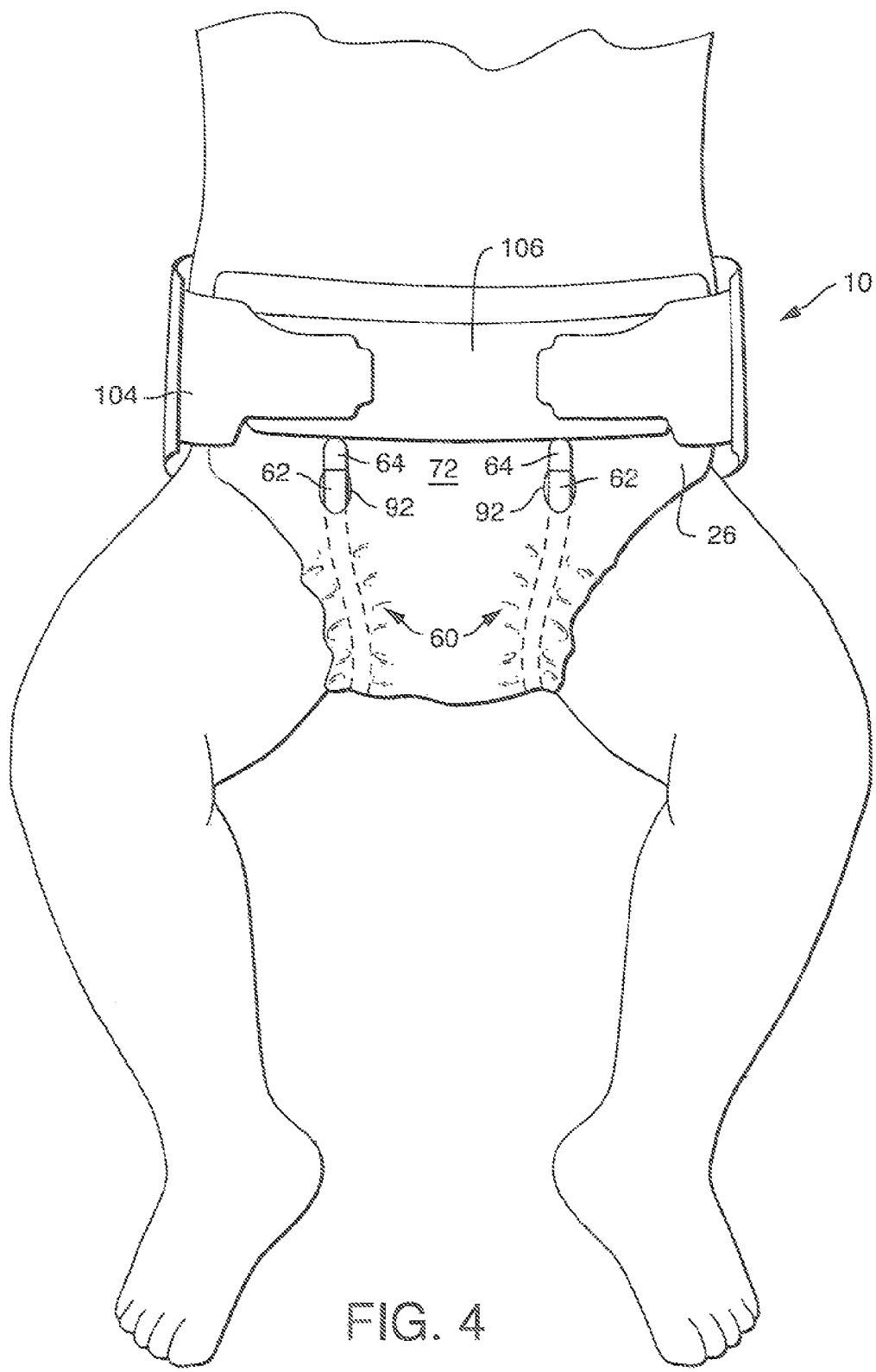
FIG. 4 is a front view of a non-limiting illustration of the absorbent article of FIG. 1, in which the waist fastening system is holding the absorbent article in a fastened condition about the lower torso of a wearer and in which the leg opening adjustment mechanisms are attached to the outer cover of the absorbent article.
Figure 5:
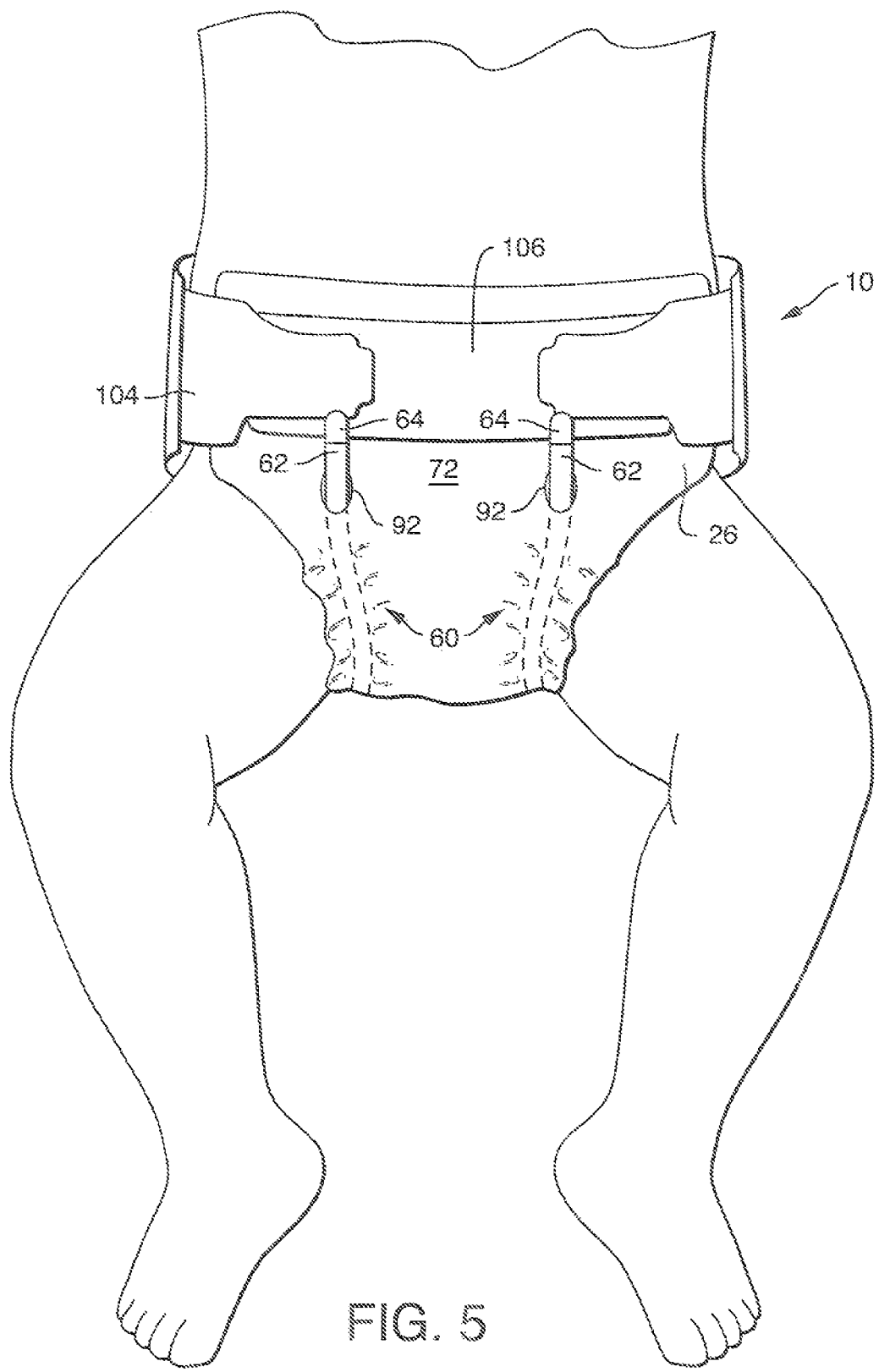
FIG. 5 is a front view of a non-limiting illustration of the absorbent article of FIG. 1, in which the waist fastening system is holding the absorbent article in a fastened condition about the lower torso of a wearer and in which the leg opening adjustment mechanisms are attached to a front fastener of the absorbent article.
Figure 6:
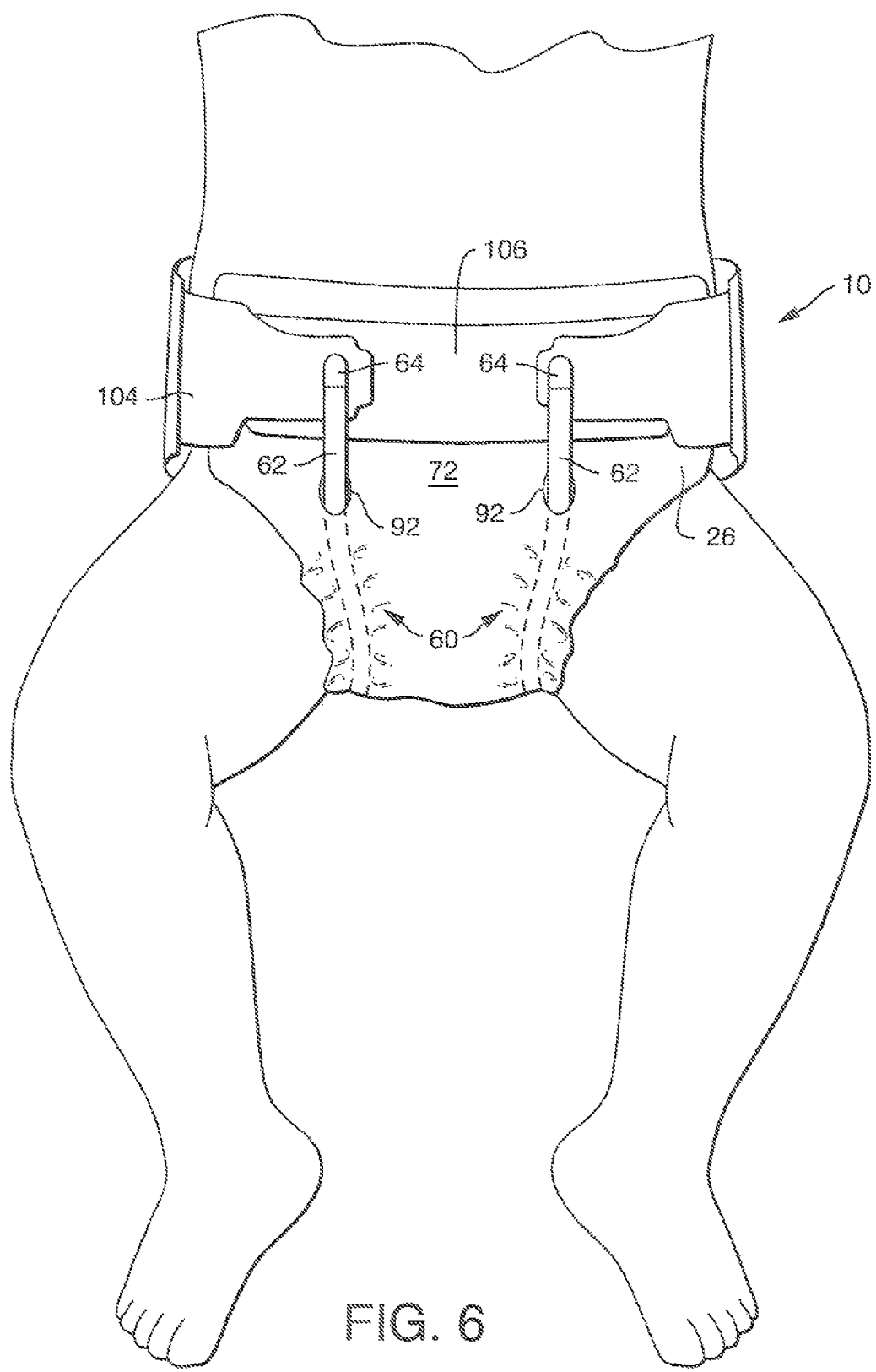
FIG. 6 is a front view of a non-limiting illustration of the absorbent article of FIG. 1, in which the waist fastening system is holding the absorbent article in a fastened condition about the lower torso of a wearer and in which the leg opening adjustment mechanisms are attached to a portion of a back fastener of the absorbent article.

The grasping tab 64 can have an absorbent article facing surface 94 which can comprise fasteners 66 which can releasably attach to the garment facing surface 100 of a cover 68 of a leg opening adjustment mechanism 60, the garment facing surface 72 of the backsheet 26, to front fastener 106, and/or to a back fastener 104 of the absorbent article 10. The fasteners 66 can be adhesives, hooks and/or loops. In an embodiment, the fasteners 66 can be a hook material such as, for example, "Velcro USA—Code HTH-877 (85-1126) 2×1 "Hook"" available from Velcro USA. In an embodiment the fasteners 66 can be repositionable such that the user of the absorbent article 10 can adjust the attachment of the fasteners 66 to the absorbent article 10 to provide the desired tension and closure of the absorbent article 10 about the legs of the wearer of the absorbent article 10. FIG. 3 is a front view of a non-limiting illustration of an absorbent article 10 in which the absorbent article 10 is in a fastened condition about the lower torso of a wearer. In the non-limiting illustration of FIG. 3, each leg opening adjustment mechanism 60 can be positioned on the body facing surface 70 of the backsheet 26 and in a non-engaged position. Each leg opening adjustment mechanism 60 can be independently adjusted by a user of the absorbent article 10. Such adjustment of the leg opening adjustment mechanism 60 by a user of the absorbent article 10 can reconfigure the leg opening adjustment mechanism 60 from a non-engaged position to an engaged position. To adjust each leg opening adjustment mechanism 60, the user can actively interact with each of the leg opening adjustment mechanisms 60 to provide a desired tension and/or closure of the absorbent article 10 in the crotch region 16 of the absorbent article 10. This can be accomplished by the user grasping a grasping tab 64 and pulling on the adjustment member 62 to extend the adjustment member 62 out of the pocket existing between the cover 68 of the leg opening adjustment mechanism 60 and the surface, such as, for example, body facing surface 70, of the backsheet 26 until the desired tension and/or closure around the wearer's leg opening has been achieved. The fasteners 66, located on an absorbent article facing surface 94 of the grasping tab 64, can be releasably attached to the garment facing surface 72 of the backsheet 26 (such as illustrated in FIG. 4), a front fastener 106 (such as illustrated in FIG. 5) and/or a back fastener 104 (such as illustrated in FIG. 6). It should be understood that the described attachment locations for the fasteners 66 can be the same for a leg opening adjustment mechanism 60 positioned on either the body facing surface 70 or the garment facing surface 72 of the backsheet 26.

Leg Elastics:

Leg elastic members, 56 and 58, can be secured to the backsheet 26, such as by being bonded thereto by laminate adhesive, generally laterally inward of the longitudinal side edges, 18 and 20, of the absorbent article 10. In an embodiment, the leg elastic members, 56 and 58, may be disposed between the inner layer 76 and outer layer 74 of the backsheet 26 or between other layers of the absorbent article 10. A wide variety of elastic materials may be used for the leg elastic members, 56 and 58. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate.

In an embodiment, the absorbent article 10 includes a pair of leg opening adjustment mechanisms 60 and leg elastic members, 56 and 58. In an embodiment, the leg elastic members, 56 and 58, can be positioned laterally outboard of the leg opening adjustment mechanisms 60 (i.e., closer in proximity to the longitudinal side edges, 18 and 20, of the absorbent article 10). In an embodiment, the leg elastic members, 56 and 58, can be positioned laterally inboard of the leg opening adjustment mechanisms 60 (i.e., the leg opening adjustment mechanisms 60 are closer in proximity to the longitudinal side edges, 18 and 20, of the absorbent article 10). In an embodiment, the leg elastic members, 56 and 58, can be positioned such that the leg elastic members, 56 and 58, at least partially overlap the leg opening adjustment mechanisms 60. In such an embodiment, the leg elastic members, 56 and 58, can be either closer in proximity to or farther in proximity from the longitudinal side edges, 18 and 20, of the absorbent article 10 when compared with the positioning of the leg opening adjustment mechanisms 60 relative to the longitudinal side edges, 18 and 20, of the absorbent article 10. In an embodiment, the leg elastic members, 56 and 58, can be positioned to completely overlap the leg opening adjustment mechanisms 60. In an embodiment of complete overlap of the leg elastic members, 56 and 58, and the leg opening adjustment mechanisms 60 and in which the leg opening adjustment mechanisms 60 can have a lateral width greater than the leg elastic members, 56 and 58, the leg elastic members, 56 and 58, can be either closer in proximity to or farther in proximity from the longitudinal side edges, 18 and 20, of the absorbent article 10 when compared with the positioning of the leg opening adjustment mechanisms 60 relative to the longitudinal side edges, 18 and 20, of the absorbent article 10. In an embodiment of complete overlap of the leg elastic members, 56 and 58, and the leg opening adjustment mechanisms 60 and in which the leg opening adjustment mechanisms 60 can have the same lateral width as the leg elastic members, 56 and 58, the leg opening adjustment mechanisms 60 and the leg elastic members, 56 and 58, can have the same proximity to each of the longitudinal side edges, 18 and 20, of the absorbent article 10. In an embodiment, the leg elastic members, 56 and 58, and the leg opening adjustment mechanisms 60 can directly contact each other. Partial overlap, or complete overlap, of the leg elastic members, 56 and 58, with the leg opening adjustment mechanisms 60, however, does not require that the leg elastic members, 56 and 58, be directly contacting each other. Partial overlap, or complete overlap, of the leg elastic members, 56 and 58, and the leg opening adjustment mechanisms 60 can occur with at least one additional material comprising the absorbent article 10 placed between the leg elastic members, 56 and 58, and the leg opening adjustment mechanisms 60.

Fastening System:

In an embodiment, the absorbent article 10 can include a fastener system. The fastener system can include one or more back fasteners 104 and one or more front fasteners 106. Portions of the fastener system may be included in the front waist region 12, back waist region 14, or both. The fastener system can be configured to secure the absorbent article 10 about the waist of the wearer and maintain the absorbent article 10 in place during use. In an embodiment, the back fasteners 104 can include one or more materials bonded together to form a composite ear as is known in the art. For example, the composite fastener may be composed of a stretch component 108, a nonwoven carrier or hook base 110, and a fastening component 112.

Waist Elastic Members:

In an embodiment, the absorbent article 10 can have waist elastic members, 52 and 54, which can be formed of any suitable elastic material. In such an embodiment, suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic members, 52 and 54, may be omitted from the absorbent article 10 without departing from the scope of this disclosure.

Figure 8:
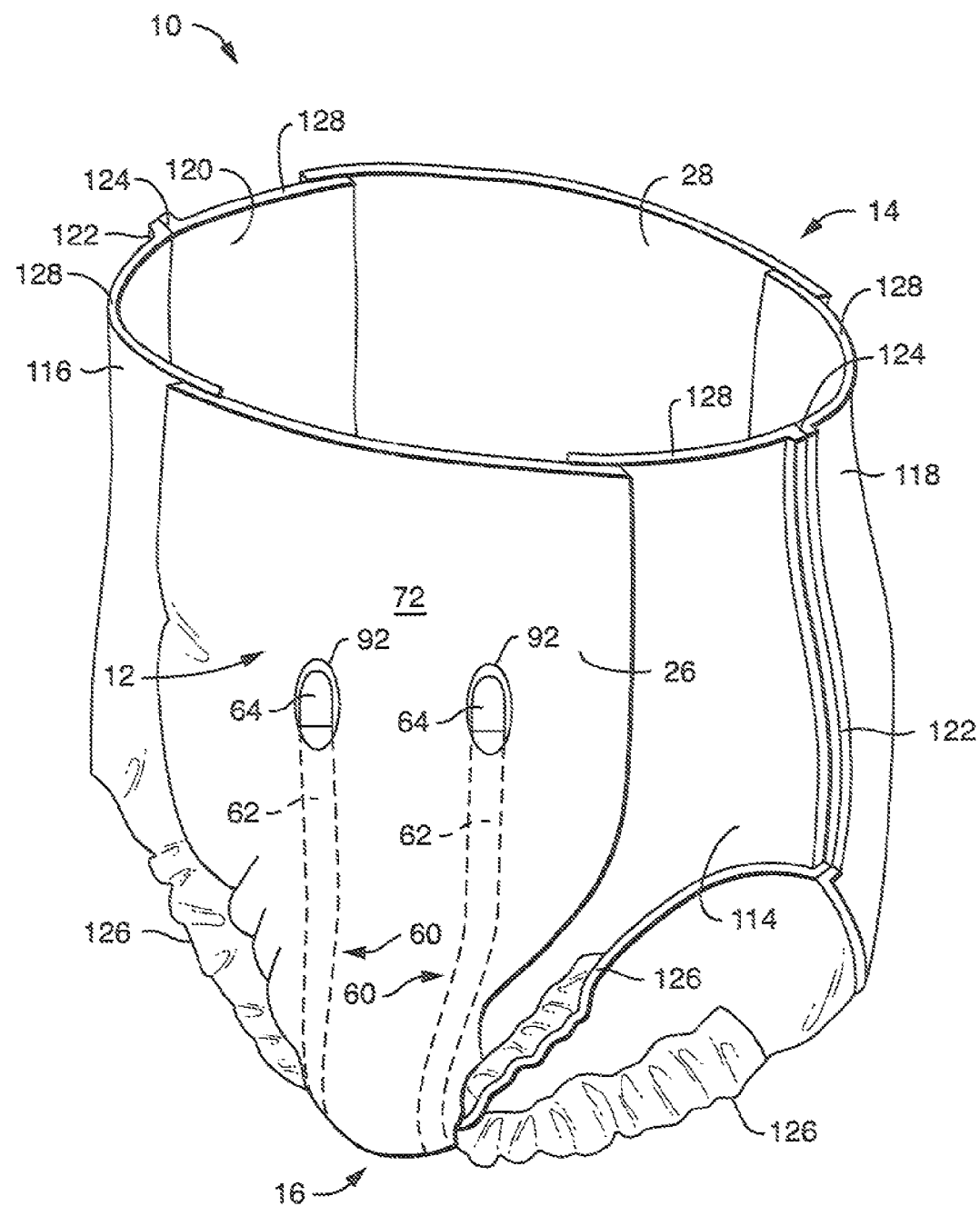
FIG. 8 is a perspective view of a non-limiting illustration of an absorbent article, such as, for example, a training pant or a youth pant.

Side Panels:

In an embodiment in which the absorbent article 10 can be a training pant, youth pant, diaper pant, or adult absorbent pant, the absorbent article 10 may have front side panels, 114 and 116, and rear side panels, 118 and 120. FIG. 8 provides a non-limiting illustration of an absorbent article 10 that can have side panels, such as front side panels, 114 and 116, and rear side panels, 118 and 120. The absorbent article 10 illustrated in FIG. 8 can also have a pair of leg opening adjustment mechanisms 60 positioned on the body facing surface 70 of the outer cover 26. The front side panels 114 and 116 and the rear side panels 118 and 120 of the absorbent article 10 can be bonded to the absorbent article 10 in the respective front and back waist regions, 12 and 14, and can extend outwardly beyond the longitudinal side edges, 18 and 20, of the absorbent article 10. In an example, the front side panels, 114 and 116, can be bonded to the inner layer 76 of the backsheet 26, such as being bonded thereto by adhesive, by pressure bonding, by thermal bonding or by ultrasonic bonding. These front side panels, 114 and 116, may also be bonded to the outer layer 74 of the backsheet 26, such as by being bonded thereto by adhesive, by pressure bonding, by thermal bonding, or by ultrasonic bonding. The back side panels, 118 and 120, may be secured to the outer and inner layers, 74 and 76 respectively, of the backsheet 26 at the back waist region 14 of the absorbent article 10 in substantially the same manner as the front side panels, 114 and 116. Alternatively, the front side panels, 114 and 116, and the back side panels, 118 and 120, may be formed integrally with the absorbent article 10, such as by being formed integrally with the backsheet 26, the body facing liner 28 or other layers of the absorbent article 10.

For improved fit and appearance, the front side panels, 114 and 116, and the back side panels, 118 and 120, can suitably have an average length measured parallel to the longitudinal axis of the absorbent article 10 that is about 20 percent or greater, and more suitably about 25 percent or greater, of the overall length of the absorbent article 10, also measured parallel to the longitudinal axis. For example, absorbent articles 10 having an overall length of about 54 centimeters, the front side panels, 114 and 116, and the back side panels, 118 and 120, suitably have an average length of about 10 centimeters or greater, and more suitably have an average length of about 15 centimeters. Each of the front side panels, 114 and 116, and back side panels, 118 and 120, can be constructed of one or more individual, distinct pieces of material. For example, each front side panel, 114 and 116, and back side panel, 118 and 120, can include first and second side panel portions (not shown) joined at a seam (not shown), with at least one of the portions including an elastomeric material. Alternatively, each individual front side panel, 114 and 116, and back side panel, 118 and 120, can be constructed of a single piece of material folded over upon itself along an intermediate fold line (not shown).

The front side panels, 114 and 116, and back side panels, 118 and 120, can each have an outer edge 122 spaced laterally from the engagement seam 124, a leg end edge 126 disposed toward the longitudinal center of the absorbent article 10, and a waist end edge 128 disposed toward a longitudinal end of the absorbent article 10. The leg end edge 126 and waist end edge 128 can extend from the longitudinal side edges, 18 and 20, of the absorbent article 10 to the outer edges 122. The leg end edges 126 of the front side panels, 114 and 116, and back side panels, 118 and 120, can form part of the longitudinal side edges, 18 and 20, of the absorbent article 10. The leg end edges 126 of the illustrated absorbent article 10 can be curved and/or angled relative to the transverse axis to provide a better fit around the wearer's legs. However, it is understood that only one of the leg end edges 126 can be curved or angled, such as the leg end edge 126 of the back waist region 14, or neither of the leg end edges 126 can be curved or angled, without departing from the scope of this disclosure. The waist end edges 128 can be parallel to the transverse axis. The waist end edges 128 of the front side panels, 114 and 116, can form part of the front waist edge 22 of the absorbent article 10, and the waist end edges 128 of the back side panels, 118 and 120, can form part of the back waist edge 24 of the absorbent article 10.

The front side panels, 114 and 116, and back side panels, 118 and 120, can include an elastic material capable of stretching laterally. Suitable elastic materials, as well as one described process for incorporating elastic front side panels, 114 and 116, and back side panels, 118 and 120, into an absorbent article 10 are described in the following U.S. Pat. No. 4,940,464 issued Jul. 10, 1990 to Van Gompel et al., U.S. Pat. No. 5,224,405 issued Jul. 6, 1993 to Pohjola, U.S. Pat. No. 5,104,116 issued Apr. 14, 1992 to Pohjola, and U.S. Pat. No. 5,046,272 issued Sep. 10, 1991 to Vogt et al.; all of which are incorporated herein by reference. As an example, suitable elastic materials include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987, in the names of Taylor et al., and PCT Application WO 01/88245 in the name of Welch et al., all of which are incorporated herein by reference. Other suitable materials are described in U.S. patent application Ser. No. 12/649,508 to Welch et al. and Ser. No. 12/023,447 to Lake et al., all of which are incorporated herein by reference. Alternatively, the front side panels, 114 and 116, and back side panels, 118 and 120, may include other woven or non-woven materials, such as those described above as being suitable for the backsheet 26 or body facing liner 28, mechanically pre-strained composites, or stretchable but inelastic materials.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a. a longitudinal direction and a lateral direction;
   b. a pair of longitudinal side edges;
   c. a body facing liner;
   d. a backsheet comprising a body facing surface and a garment facing surface;
   e. a pair of leg opening adjustment mechanisms positioned on the body facing surface of the backsheet and each leg opening adjustment mechanism comprising:
      i. a cover comprising two longitudinal direction edges and two lateral direction edges; and
      ii. an adjustment member comprising a bonded end and an unbonded end;
   f. a pair of leg elastic members; and
   g. an absorbent body positioned between the body facing liner and the backsheet.

2. The absorbent article of claim 1 wherein both of the longitudinal direction edges of the cover and at least one of the lateral direction edges of the cover is bonded to the body facing surface of the backsheet to create a pocket between the cover and the body facing surface of the backsheet, the adjustment member being positioned within the pocket.

3. The absorbent article of claim 2 wherein both of the lateral direction edges of the cover are bonded to the body facing surface of the backsheet to create the pocket between the cover and the body facing surface of the backsheet, the adjustment member being fully enclosed within the pocket, and wherein the backsheet further comprises an opening through which the unbonded end of the adjustment member can extend.

4. The absorbent article of claim 1 wherein the leg opening adjustment mechanisms are positioned laterally inward of the longitudinal side edges.

5. The absorbent article of claim 1 wherein the leg elastic members are positioned laterally inward of the longitudinal side edges.

6. The absorbent article of claim 1 wherein the leg opening adjustment mechanisms partially overlap the leg elastic members.

7. The absorbent article of claim 1 wherein the leg elastic members are closer in proximity to the longitudinal side edges than the leg opening adjustment mechanisms.

8. The absorbent article of claim 1 wherein the leg opening adjustment mechanisms are closer in proximity to the longitudinal side edges than the leg elastic members.

9. The absorbent article of claim 1 wherein the backsheet further comprises an opening through which the unbonded end of the adjustment member can extend.

10. The absorbent article of claim 1 wherein the adjustment member further comprises a grasping tab, the grasping tab comprising fasteners.

11. The absorbent article of claim 1 wherein the leg opening adjustment mechanisms are positioned laterally outward of the absorbent body.

12. An absorbent article comprising:
    a. a longitudinal direction and a lateral direction;
    b. a pair of longitudinal side edges;
    c. a body facing liner;
    d. a backsheet comprising a body facing surface and a garment facing surface;
    e. a pair of leg opening adjustment mechanisms positioned on the garment facing surface of the backsheet and each leg opening adjustment mechanism comprising:
       i. a cover comprising two longitudinal direction edges and two lateral direction edges, both of the longitudinal direction edges and at least one of the lateral direction edges of the cover being bonded to the garment facing surface of the backsheet to create a pocket between the cover and the garment facing surface of the backsheet; and
       ii. an adjustment member comprising a bonded end and an unbonded end, the adjustment member being positioned within the pocket;
    f. a pair of leg elastic members; and
    g. an absorbent body positioned between the body facing liner and the backsheet.

13. The absorbent article of claim 12 wherein the leg opening adjustment mechanisms are positioned laterally inward of the longitudinal side edges.

14. The absorbent article of claim 12 wherein the leg elastic members are positioned laterally inward of the longitudinal side edges.

15. The absorbent article of claim 12 wherein the leg opening adjustment mechanisms partially overlap the leg elastic members.

16. The absorbent article of claim 12 wherein the leg elastic members are closer in proximity to the longitudinal side edges than the leg opening adjustment mechanisms.

17. The absorbent article of claim 12 wherein the leg opening adjustment mechanisms are closer in proximity to the longitudinal side edges than the leg elastic members.

18. The absorbent article of claim 12 wherein the adjustment member further comprises a grasping tab, the grasping tab comprising fasteners.

19. The absorbent article of claim 12 wherein the leg opening adjustment mechanisms are positioned laterally outward of the absorbent body.

* * * * *